(12) United States Patent
Chen et al.

(10) Patent No.: US 7,799,440 B2
Chen et al.
(45) Date of Patent: Sep. 21, 2010

(54) ORGANIC ELECTROLUMINESCENT DEVICE AND HOST MATERIAL OF LUMINESCENT AND HOLE-BLOCKING MATERIAL THEREOF

(75) Inventors: Ruey-min Chen, Taiwan (TW); Chung-yu Chen, Taiwan (TW); Chin-in Wu, Taiwan (TW); Wu-jen Hsieh, Taiwan (TW)

(73) Assignee: Chi Mei Optoelectronics Corp., Tainan County (TW)

( * ) Notice: Subject to any disclaimer, the term of this patent is extended or adjusted under 35 U.S.C. 154(b) by 1110 days.

(21) Appl. No.: 11/482,199

(22) Filed: Jul. 7, 2006

(65) Prior Publication Data
US 2007/0015005 A1     Jan. 18, 2007

(30) Foreign Application Priority Data
Jul. 7, 2005  (TW) ................ 94122965 A

(51) Int. Cl.
H01L 51/54  (2006.01)
(52) U.S. Cl. ............ 428/690; 428/917; 313/504; 313/506; 585/27; 257/102; 257/E51.001; 257/E51.024; 257/E51.032
(58) Field of Classification Search ......... 428/690, 428/917; 313/504, 506; 585/27; 257/E51.001, 257/E51.018, E51.024, E51.032
See application file for complete search history.

(56) References Cited

U.S. PATENT DOCUMENTS

| | | | |
|---|---|---|---|
| 7,241,513 B2 | 7/2007 | Suzuki et al. | |
| 7,338,721 B2 * | 3/2008 | Suzuki et al. | 428/690 |
| 7,482,490 B2 * | 1/2009 | Nishiyama et al. | 564/308 |
| 7,510,781 B2 * | 3/2009 | Suzuki et al. | 428/690 |
| 7,691,492 B2 * | 4/2010 | Yamada et al. | 428/690 |
| 2003/0118866 A1 * | 6/2003 | Oh et al. | 428/690 |
| 2006/0008672 A1 * | 1/2006 | Jarikov | 428/690 |
| 2006/0269781 A1 * | 11/2006 | Lai et al. | 428/690 |
| 2007/0212568 A1 * | 9/2007 | Wang | 428/690 |

FOREIGN PATENT DOCUMENTS

| | | |
|---|---|---|
| CN | 1571763 | 1/2005 |
| JP | 10095972 A * | 4/1998 |
| JP | 2001196177 A * | 7/2001 |
| JP | 2005044791 A * | 2/2005 |
| JP | 2006131782 A * | 5/2006 |

OTHER PUBLICATIONS

Cao et al. Journal of Organometallic Chemistry 689 (2004) 2201-2206.*
Machine Translation of JP 10-095972 A.*
Machine Translation of JP 2001-196177 A.*
Machine Translation of JP 2005-044791 A.*
Machine Translation of JP 2006-131782 A.*
STIC search results.*

* cited by examiner

*Primary Examiner* — David Wu
*Assistant Examiner* — Vu A Nguyen

(57) ABSTRACT

An organic electroluminescent device including an anode on a substrate, an organic luminescent layer on the anode and a cathode on the organic luminescent layer is provided. The luminescent layer contains a fluorene compound as formula (1):

Formula (1):

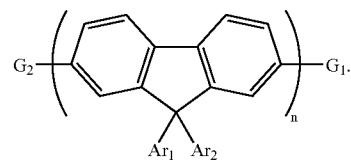

19 Claims, 6 Drawing Sheets

ORGANIC ELECTROLUMINESCENT DEVICE AND HOST MATERIAL OF LUMINESCENT AND HOLE-BLOCKING MATERIAL THEREOF

CROSS REFERENCE TO RELATED APPLICATIONS

The present application is based on and claims priority from Taiwan Patent Appln. No. 094122965 filed on Jul. 7, 2005, the disclosure of which is hereby incorporated by reference in its entirety.

BACKGROUND OF THE INVENTION

1. Field of the Invention

The invention relates to an electroluminescent device, and more particularly, to a host material of the luminescent layer and a hole-blocking material of the electroluminescent device.

2. Description of the Prior Art

In recent history, displays having the characteristics of light weight and high performance, such as liquid crystal displays have become increasingly popular. Nevertheless, problems including narrow viewing angle and slow response rate are still found in most liquid crystal displays, therefore the LCD can not use for displaying high speed moving pictures. The requirement for the backlight of LCD will cause more power consumption. Moreover, the fabrication of large-scale liquid crystal display panels is still difficult to achieve.

Consequently, organic electroluminescent displays have been developed to overcome the aforementioned disadvantage of liquid crystal displays.

In general, organic electroluminescent displays are devices utilizing the property of organic luminescent materials to generate light. An organic electroluminescent device is primarily composed of a pair of electrodes and an organic luminescent layer. The organic luminescent layer includes luminescent materials. When a current passes through a transparent anode and metallic cathode of the device, electrons and holes within the luminescent material will combine and generate exciton, thereby inducing the luminescent material to illuminate and produce light.

However, some problems are found in most organic electroluminescent devices today. Problems arising are especially related to the stability and efficiency of the luminescent material. Recently, luminescent materials used in electroluminescent devices to fabricate the luminescent layer include a host material of tris(8-quinolinol)aluminum ($AlQ_3$) and a doped guest material of a fluorescent material, or a host material of 4,4'-N,N'-dicarbazole-biphenyl (CBP) and a doped guest material of a phosphorescent material. The luminance efficiency is generally higher when utilizing a doped guest material of phosphorescent material than when utilizing the fluorescent material. However, the CBP being utilized will easily induce a crystallization phenomenon, in which the phenomenon will not only reduce the brightness of the electroluminescent device, but also significantly shorten the life expectancy of the device.

SUMMARY OF THE INVENTION

It is therefore an objective of the present invention to provide a host material for the luminescent layer of the organic electroluminescent device, in which the host material possesses a film characteristic which does not readily crystallize.

It is another aspect of the present invention to provide a hole-blocking material for satisfying the need of fabricating full color organic electroluminescent devices.

It is another aspect of the present invention to provide an electroluminescent device having longer life expectancy.

According to the present invention, a host material of a luminescent layer applicable in an organic electroluminescent device is disclosed, in which the host material includes a fluorene compound as formula (1):

Formula (1):

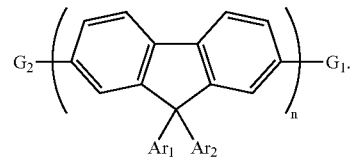

Preferably, Ar1 and Ar2 each comprises a replaceable aryl group having 6 to 12 carbon atoms; and G1 and G2 each comprises a replaceable aryl group having 6 to 24 carbon atoms, a replaceable amino group, a replaceable boron group, or a silyl group having 3 to 18 carbon atoms, in which n is an integer between 1 to 4.

According to a preferred embodiment of the present invention, the replaceable aryl group of Ar1 and Ar2 is selected from the group consisting of phenyl, biphenyl, tolyl, naphthyl, anthranyl, and phenanthryl.

According to a preferred embodiment of the present invention, the replaceable amino group comprises a replaceable aryl group having 6 to 24 carbon atoms.

According to a preferred embodiment of the present invention, the replaceable boron group comprises a replaceable aryl group having 6 to 12 carbon atoms.

According to a preferred embodiment of the present invention, the luminescent layer further comprises a dopant, in which the dopant is selected from the group consisting of at least two of $FIr(pic)_3$, $Ir(ppy)_3$, $Ir(m\text{-}ppy)_3$, $Ir(btp)_2(acac)$, $Ir(btp)_3$, $Ir(DBQ)_2(acac)$, PtOEP, $Ir(tpy)_2(pz2BEt2)$, $Ir(tpy)_2(pz2BPh2)$, $Ir(piq)_2(acac)$, $Ir(piq\text{-}F)_2(acac)$, $Ir(pbq\text{-}F)_2(acac)$, $Ir(piq\text{-}F)_3$, $Ir(piq)_3$, and $Ir(pbq)_3$, and the formula of the dopants comprises:

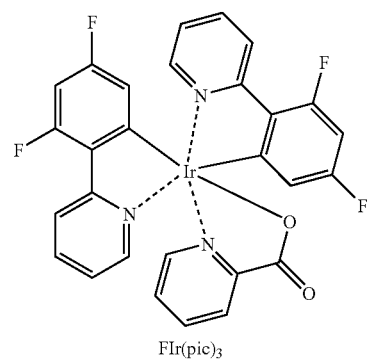

FIr(pic)₃

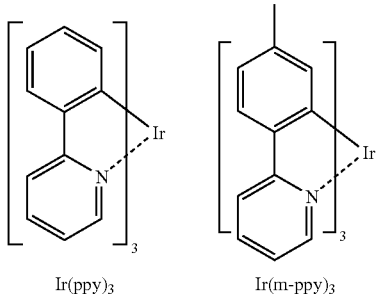

Ir(ppy)₃     Ir(m-ppy)₃

-continued
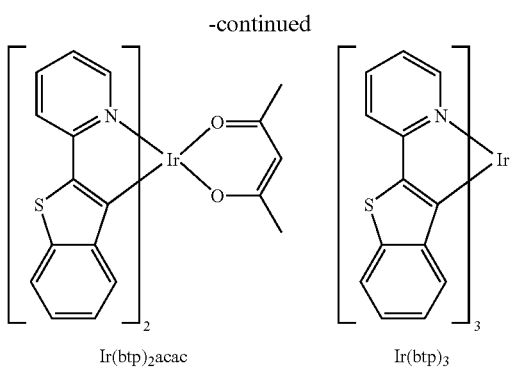
Ir(btp)₂acac          Ir(btp)₃
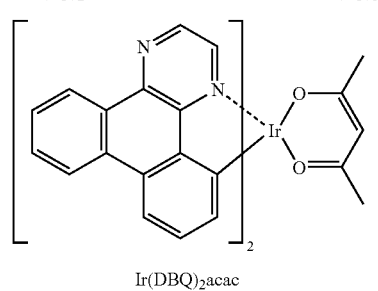
Ir(DBQ)₂acac
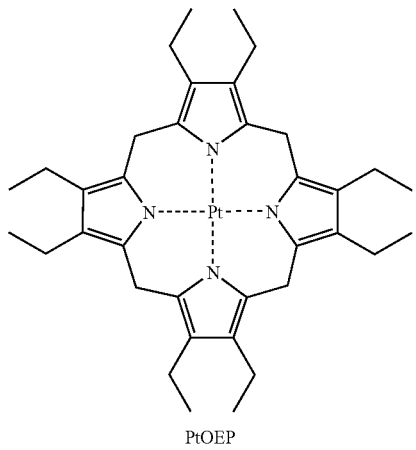
PtOEP
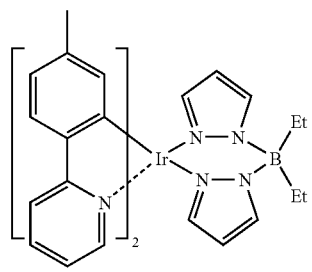
Ir(tpy)₂(pz2BEt2)
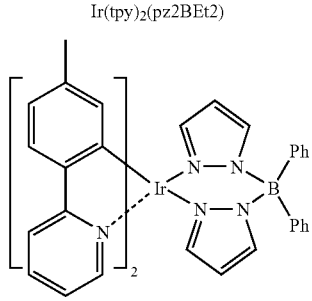
Ir(tpy)₂(pz2BPh2)
-continued
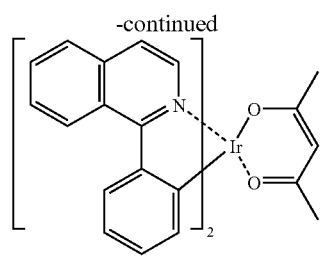
Ir(piq)₂(acac)
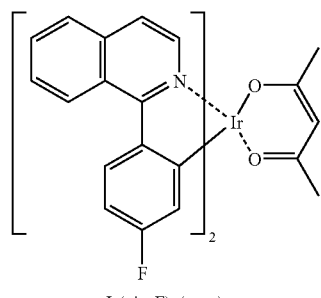
Ir(piq-F)₂(acac)
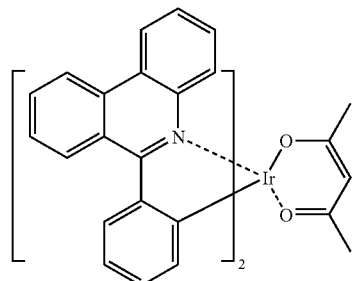
Ir(pbq-F)₂(acac)
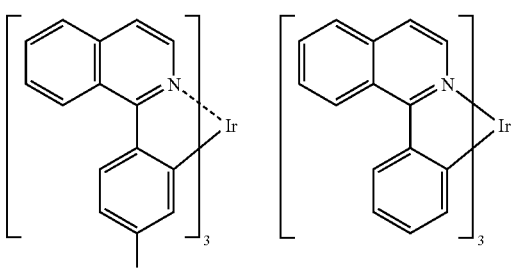
Ir(piq-F)₃          Ir(piq)₃
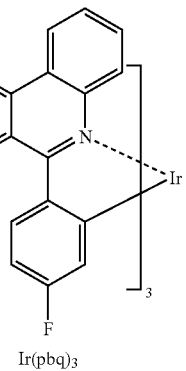
Ir(pbq)₃
According to one aspect of the present invention, a hole-blocking material applicable in an organic electroluminescent device is disclosed, in which the hole-blocking material comprises a fluorene compound as formula (1):

Formula (1):

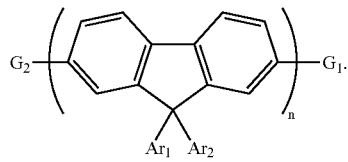

Preferably, Ar1 and Ar2 each comprises a replaceable aryl group having 6 to 12 carbon atoms; and G1 and G2 each comprises a replaceable aryl group having 6 to 24 carbon atoms, a replaceable amino group, a replaceable boron group, or a silyl group having 3 to 18 carbon atoms, in which n is an integer between 1 to 4.

According to a preferred embodiment of the present invention, the replaceable aryl group of Ar1 and Ar2 is selected from the group consisting of phenyl; biphenyl, tolyl, naphthyl, anthranyl, and phenanthryl.

According to a preferred embodiment of the present invention, the replaceable amino group comprises a replaceable aryl group having 6 to 24 carbon atoms.

According to a preferred embodiment of the present invention, the replaceable boron group comprises a replaceable aryl group having 6 to 12 atoms.

According to one aspect of the present invention, an electroluminescent device is disclosed, in which the electroluminescent device is composed of a substrate; an anode, disposed on the substrate; an organic luminescent layer, disposed on the anode; and a cathode, disposed on the organic luminescent layer. The organic luminescent layer comprises a fluorene compound as formula (1): Formula (1):

Formula (1):

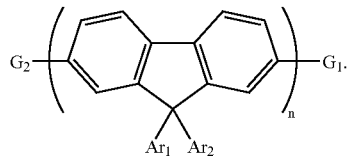

Preferably, Ar1 and Ar2 each comprises a replaceable aryl group having 6 to 12 carbon atoms; and G1 and G2 each comprises a replaceable aryl group having 6 to 24 carbon atoms, a replaceable amino group, a replaceable boron group, or a silyl group having 3 to 18 atoms, in which n is an integer between 1 to 4.

According to a preferred embodiment of the present invention, the replaceable aryl group of Ar1 and Ar2 is selected from the group consisting of phenyl; biphenyl, tolyl, naphthyl, anthranyl, and phenanthryl.

According to a preferred embodiment of the present invention, the replaceable amino group comprises a replaceable aryl group having 6 to 24 carbon atoms.

According to a preferred embodiment of the present invention, the replaceable boron group comprises a replaceable aryl group having 6 to 12 carbon atoms.

According to a preferred embodiment of the present invention, the electroluminescent device described above further includes a hole-blocking layer disposed between the cathode and the organic luminescent layer, in which the hole-blocking layer comprises the compound of formula (1).

According to a preferred embodiment of the present invention, the electroluminescent device described above further includes an electron transport layer disposed between the hole-blocking layer and the cathode.

According to a preferred embodiment of the present invention, the electroluminescent device described above further includes an electron injection layer, disposed between the electron transport layer and the cathode.

According to a preferred embodiment of the present invention, the electroluminescent device described above further includes a hole transport layer, disposed between the anode and the organic luminescent layer.

According to a preferred embodiment of the present invention, the electroluminescent device described above further includes a hole injection layer, disposed between the anode and the hole transport layer.

According to a preferred embodiment of the present invention, the organic luminescent layer further comprises a dopant, in which the dopant is selected from the group consisting of at least two of $FIr(pic)_3$, $Ir(ppy)_3$, $Ir(m-ppy)_3$, $Ir(btp)_2(acac)$, $Ir(btp)_3$, $Ir(DBQ)_2(acac)$, PtOEP, $Ir(tpy)_2(pz2BEt2)$, $Ir(tpy)_2(pz2BPh2)$, $Ir(piq)_2(acac)$, $Ir(piq-F)_2(acac)$, $Ir(pbq-F)_2(acac)$, $Ir(piq-F)_3$, $Ir(piq)_3$, and $Ir(pbq)_3$, and the formula of the dopants comprises:

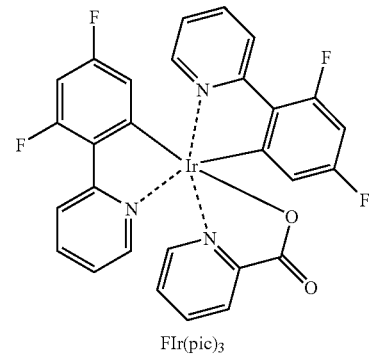

FIr(pic)₃

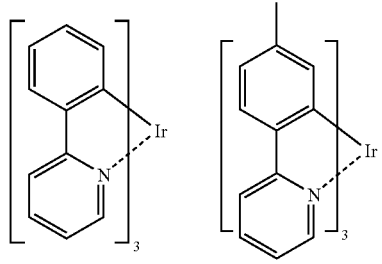

Ir(ppy)₃  Ir(m-ppy)₃

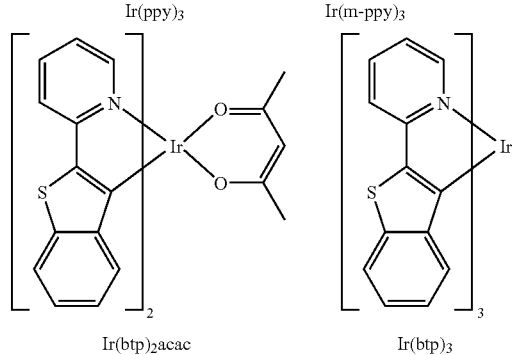

Ir(btp)₂acac  Ir(btp)₃

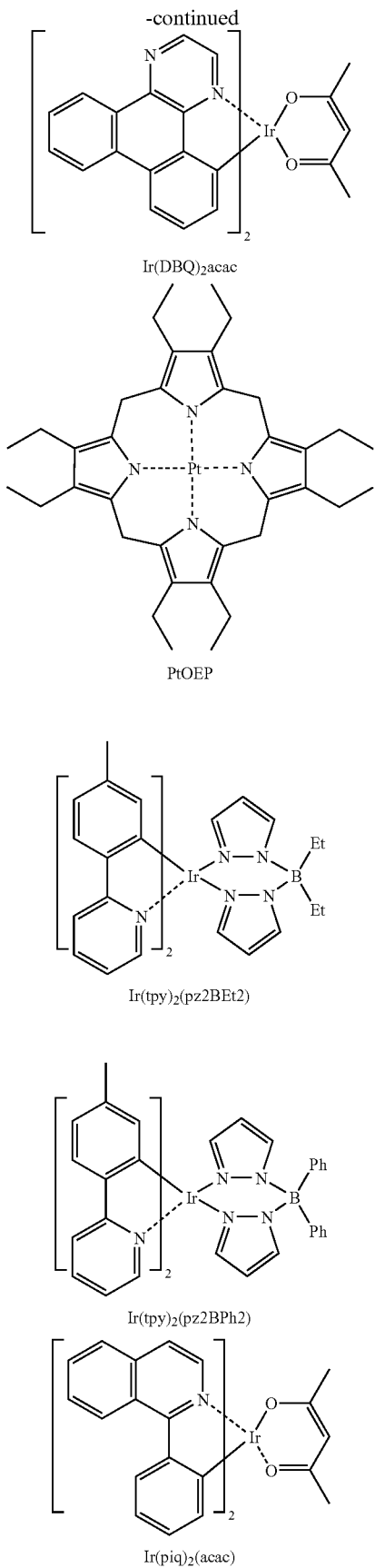
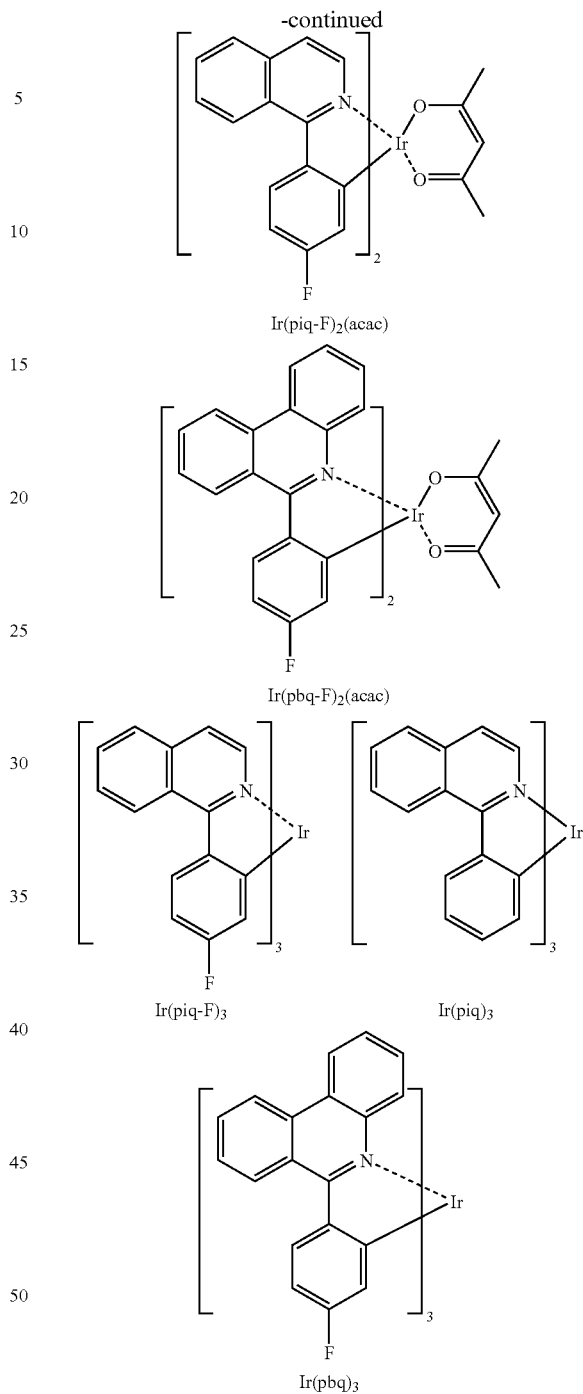

By utilizing the material of the present invention to fabricate the organic luminescent layer of the organic electroluminescent device, the device will not only have the advantage of high thermal stability, but also have improved luminance performance. The material disclosed by the present invention also applies to organic light emitting diode displays. Specifically, the film characteristic of the material further increases the luminance performance and life expectancy of the device. This effect is possible because the material does not crystallize easily. Thereby, the luminance performance can be increased significantly by incorporating the material of the present invention into the hole-blocking layer of the electroluminescent device.

These and other objectives of the present invention will no doubt become obvious to those of ordinary skill in the art after reading the following detailed description of a preferred embodiment that is illustrated in the various figures and drawings.

DETAILED DESCRIPTION OF EXEMPLARY EMBODIMENTS

Figure 1:
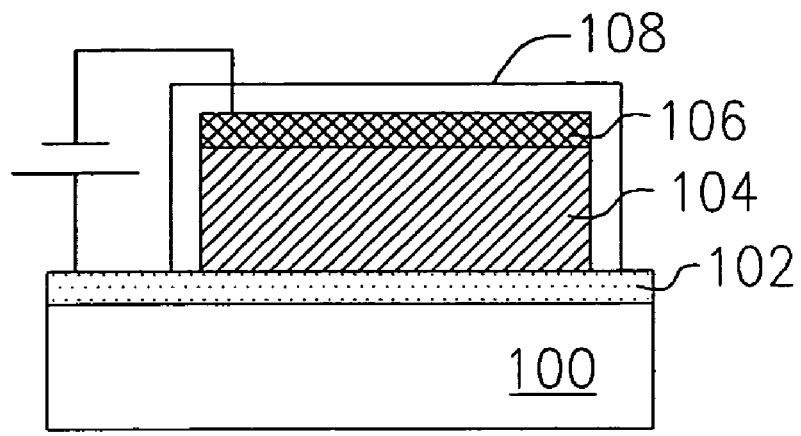
FIG. 1 is a perspective diagram showing a cross-section of an electroluminescent device according to an embodiment of the present invention.

FIG. 1 is a perspective diagram showing a cross-section of an electroluminescent device according to an embodiment of the present invention.

As shown in FIG. 1, the electroluminescent device is a light emitting diode having a single layer organic structure, in which the light emitting diode includes a transparent substrate 100, an anode 102, an organic luminescent layer 104, a cathode 106, and a passivation layer 108. The transparent substrate 100 can be a glass substrate, plastic substrate, or flexible substrate. The anode 102 is disposed on the transparent substrate 100. The anode 102 is utilized to provide holes for injecting into the organic luminescent layer 104, in which the anode 102 includes a work function of 4.5 eV or above. Preferably, the anode 102 is composed of indium tin oxide (ITO), tin oxide, gold, silver, platinum, or copper.

The organic luminescent layer 104 is disposed on the anode 102. Specifically, the material of the organic luminescent layer 104 highlights the characteristics of the present invention, in which the chemical formula of the layer and fabrication thereof will be discussed later in this disclosure.

The cathode 106 is disposed on the organic luminescent layer 104. The cathode 106 is utilized to provide electrons for injecting into the organic luminescent layer 104, in which the cathode 106 includes a relatively weaker work function. Preferably, the cathode 106 is composed of indium, aluminum, magnesium indium alloy, magnesium aluminum alloy, magnesium lithium alloy, or magnesium silver alloy.

The passivation layer 108 covers the electroluminescent device entirely, in which the passivation layer 108 functions as a sealing film to prevent external water vapors from entering the electroluminescent device.

Most electrical currents applied to the electroluminescent device are direct currents, pulse currents, or alternating currents. Additionally, the luminescence of the electroluminescence device can be either transmitting, which light is transmitted through the anode 102, or reflecting, which light is transmitted through the cathode 106.

Figure 2:
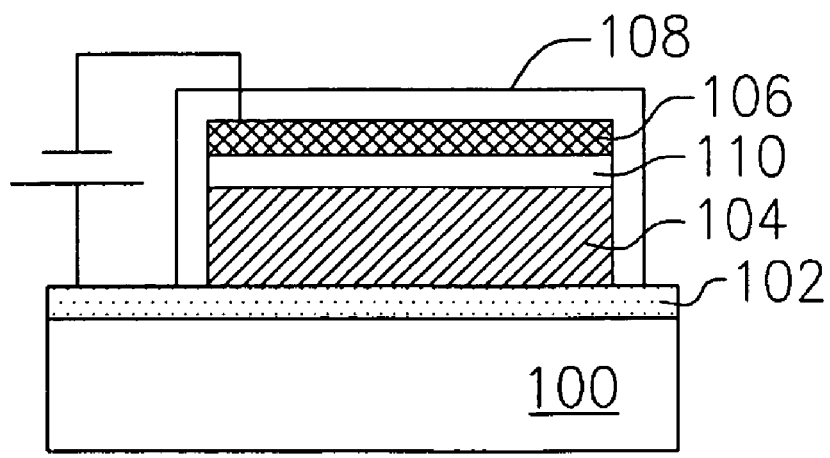
FIG. 2 is a perspective diagram showing a cross-section of an electroluminescent device according to another embodiment of the present invention.
Figure 3:
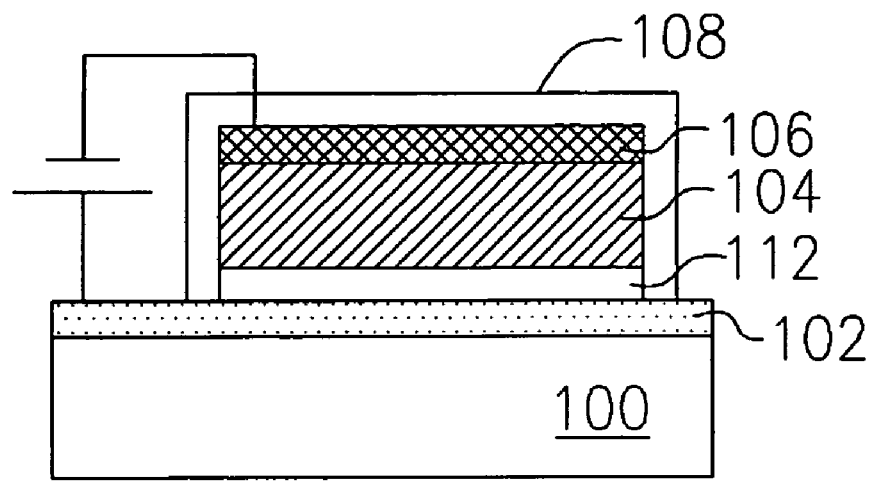
FIG. 3 is a perspective diagram showing a cross-section of an electroluminescent device according to another embodiment of the present invention.

According to another embodiment of the present invention, the electroluminescent device can be an organic light emitting diode having a double layer organic structure, as shown in FIG. 2 and FIG. 3. As shown in FIG. 2, the light emitting diode includes an electron transport layer 110 between the organic luminescent layer 104 and the cathode 106. The light emitting diode having a double layer structure in FIG. 3 on the other hand, includes a hole transport layer 112 between the organic luminescent layer 104 and the anode 102.

Figure 4:
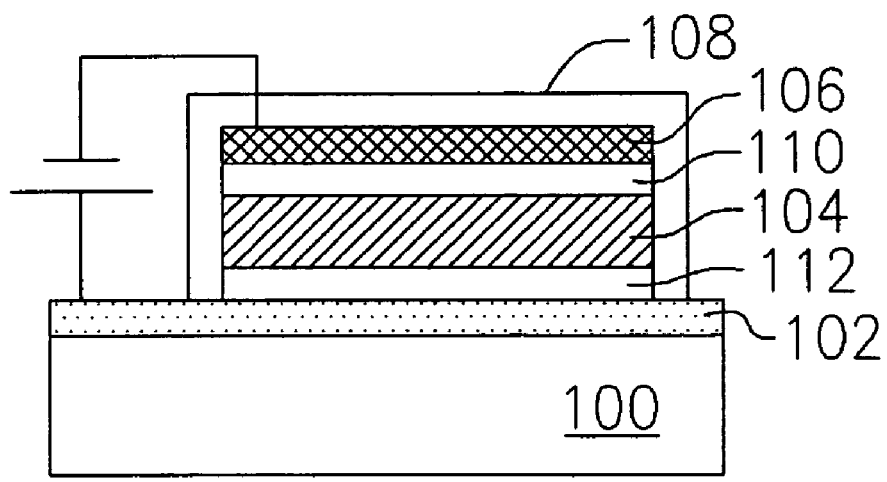
FIG. 4 is a perspective diagram showing a cross-section of an electroluminescent device according to another embodiment of the present invention.

According to another embodiment of the present invention, the electroluminescent device can be an organic light emitting diode having a triple layer organic structure. As shown in FIG. 4, in addition to the electron transport layer 110 disposed between the organic luminescent layer 104 and the cathode 106, the light emitting diode further includes a hole transport layer 112 between the organic luminescent layer 104 and the anode 102.

Figure 5:
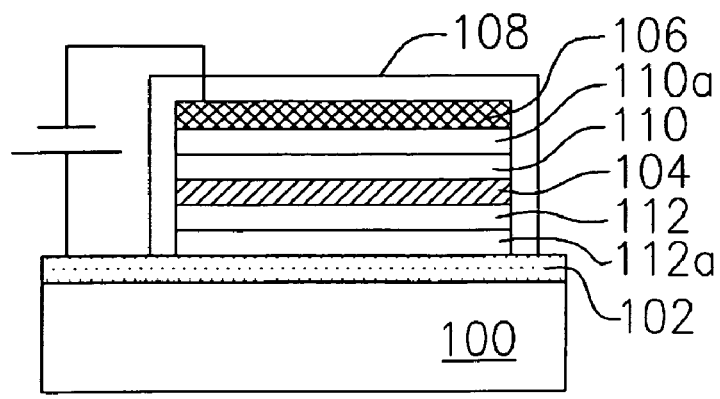
FIG. 5 is a perspective diagram showing a cross-section of an electroluminescent device according to another embodiment of the present invention.

According to another embodiment of the present invention, the electroluminescent device can be an organic light emitting diode having a five layer organic structure. As shown in FIG. 5, in addition to the electron transport layer 110 disposed between the organic luminescent layer 104 and the cathode 106, the organic light emitting diode having the five layer organic structure includes an electron injection layer 110a between the cathode 106 and the electron transport layer 110. Moreover, in addition to the hole transport layer 112 disposed between the organic luminescent layer 104 and the anode 102, a hole injection layer 112a is disposed between the anode 102 and the hole transport layer 112.

Figure 6:
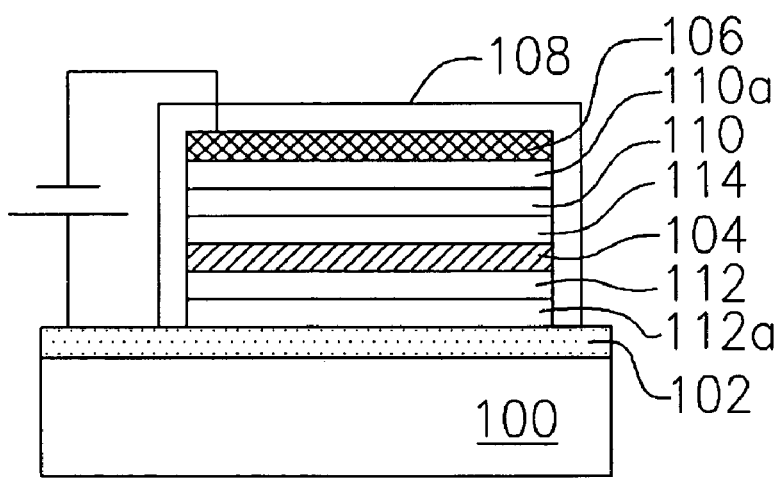
FIG. 6 is a perspective diagram showing a cross-section of an electroluminescent device according to another embodiment of the present invention.

According to another embodiment of the present invention, the electroluminescent device can be an organic light emitting diode having a six layer organic structure. As shown in FIG. 6, in addition to the electron transport layer 110 disposed between the organic luminescent layer 104 and the cathode 106, an electron injection layer 110a is disposed between the cathode 106 and the electron transport layer 110. The six layer organic structure of the organic light emitting diode also includes a hole transport layer 112 between the organic luminescent layer 104 and the anode 102, and a hole injection layer 112a between the anode 102 and the hole transport layer 112. Additionally, a hole-blocking layer 114 is disposed between the electron injection layer 110a and the organic luminescent layer 104. The hole-blocking layer 114 serves to stop the holes in the organic luminescent layer 104, thereby increasing the luminescent efficiency of the device. Moreover, the host material of the organic luminescent layer 104 can be applied in the hole-blocking layer 114 as a hole-blocking material. The chemical structure and fabrication method of the host material is explained below.

The host material of the organic luminescent layer 104 is the primary characteristic of the present invention. The host material is discussed in detail below.

The host material of the organic luminescent layer 104 also serves as a hole-blocking material, in which the hole-blocking material is a compound having fluorene as a basic structure. The molecular structure of the compound is shown in formula (1) below:

Formula (1):

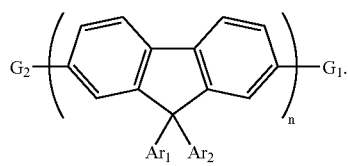

In Formula (1), Ar1 and Ar2 each represents a replaceable aryl group having 6 to 12 carbon atoms, and G1 and G2 each represents a replaceable aryl group having 6 to 24 carbon atoms, a replaceable amino group, a replaceable boron group, or a silyl group having 3 to 18 carbon atoms, in which n is an integer between 1 to 4.

The replaceable aryl group of Ar1 and Ar2 is selected from the group consisting of: phenyl, biphenyl, tolyl, naphthyl, anthranyl, and phenanthryl.

The replaceable amino group includes a replaceable aryl group having 6 to 24 carbon atoms, and the replaceable boron group includes a replaceable aryl group having 6 to 12 carbon atoms.

Embodiments regarding compounds derived from the structure of Formula (1) are listed below, in which the compounds can be applied in the electroluminescent device of the present invention. However, the compounds are not limited to the structure provided from Formula (1).

(i) Ar1 and Ar2 each represents a replaceable aryl group having 6 to 12 carbon atoms, and G1 and G2 each represents a replaceable aryl group having 6 to 24 carbon atoms.

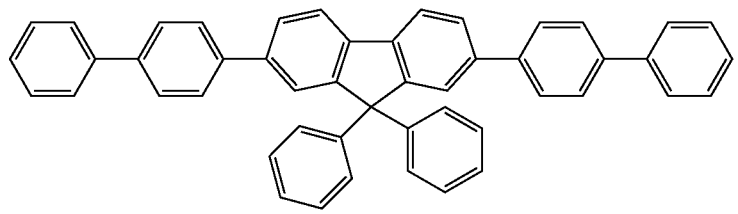

(2-1)

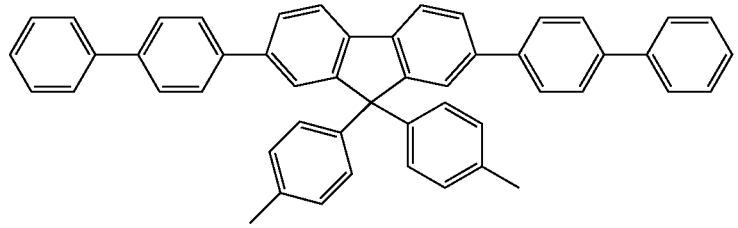

(2-2)

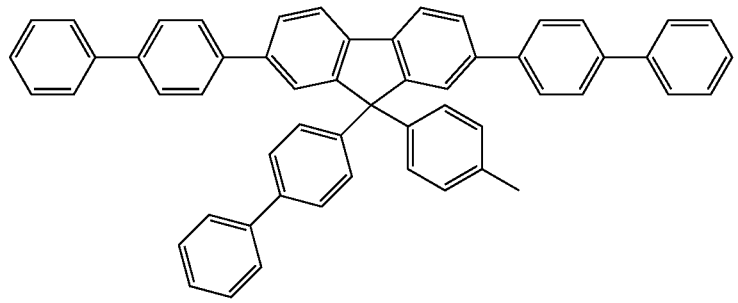

(2-3)

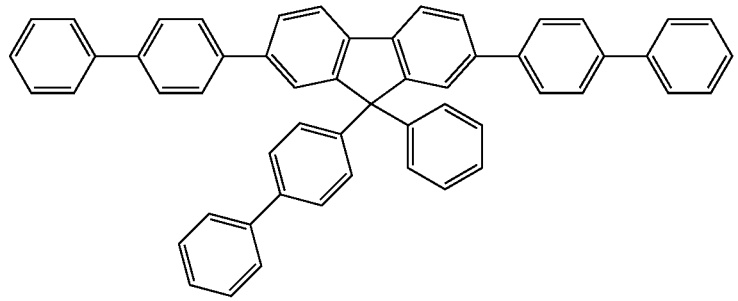

(2-4)

-continued
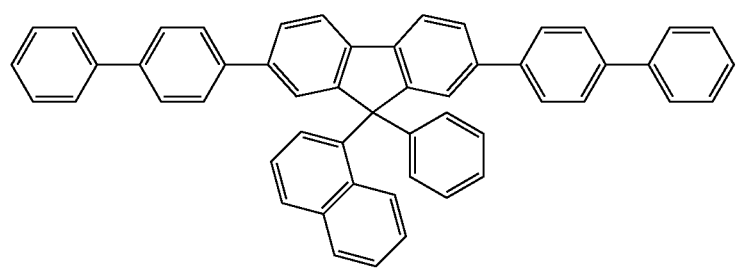
(2-5)
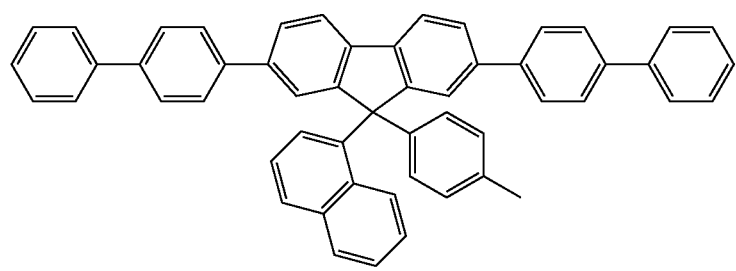
(2-6)
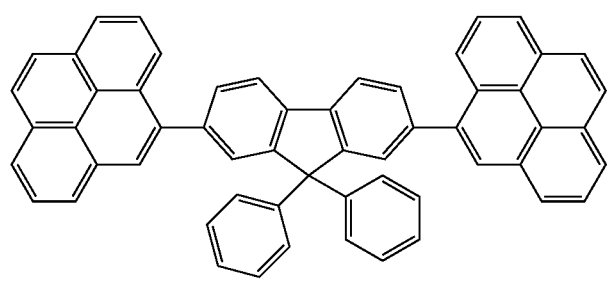
(2-7)
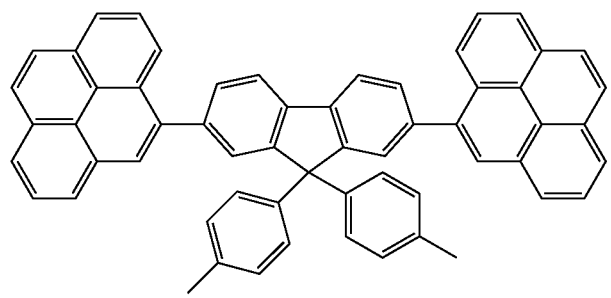
(2-8)
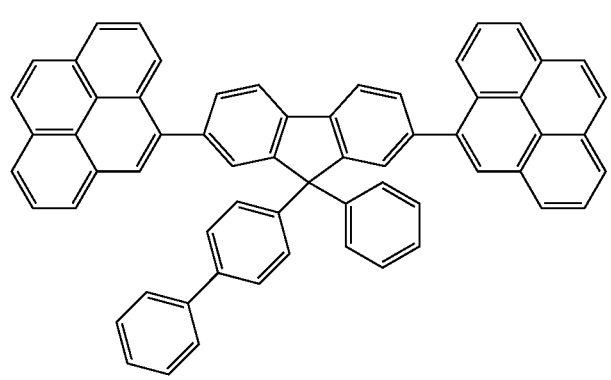
(2-9)

-continued
(2-10)
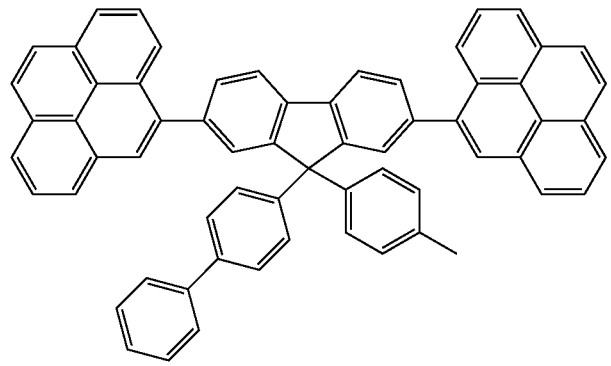
(2-11)
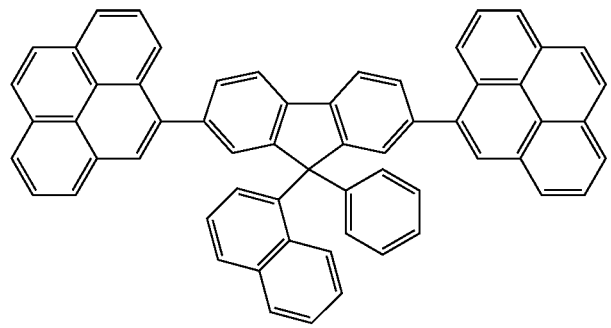
(2-12)
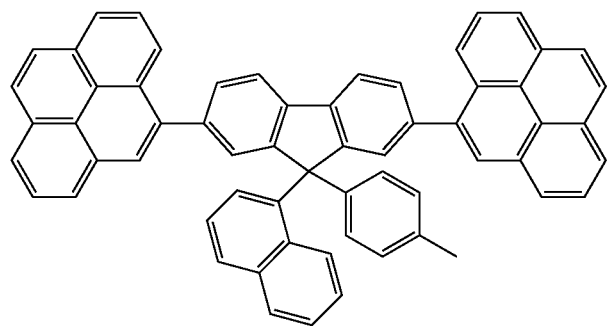
(2-13)
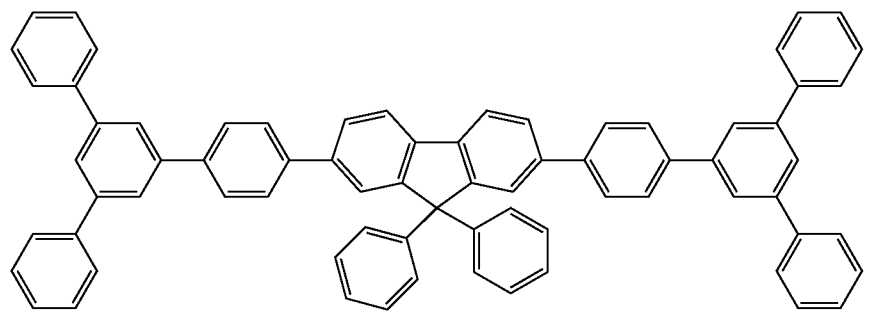

-continued
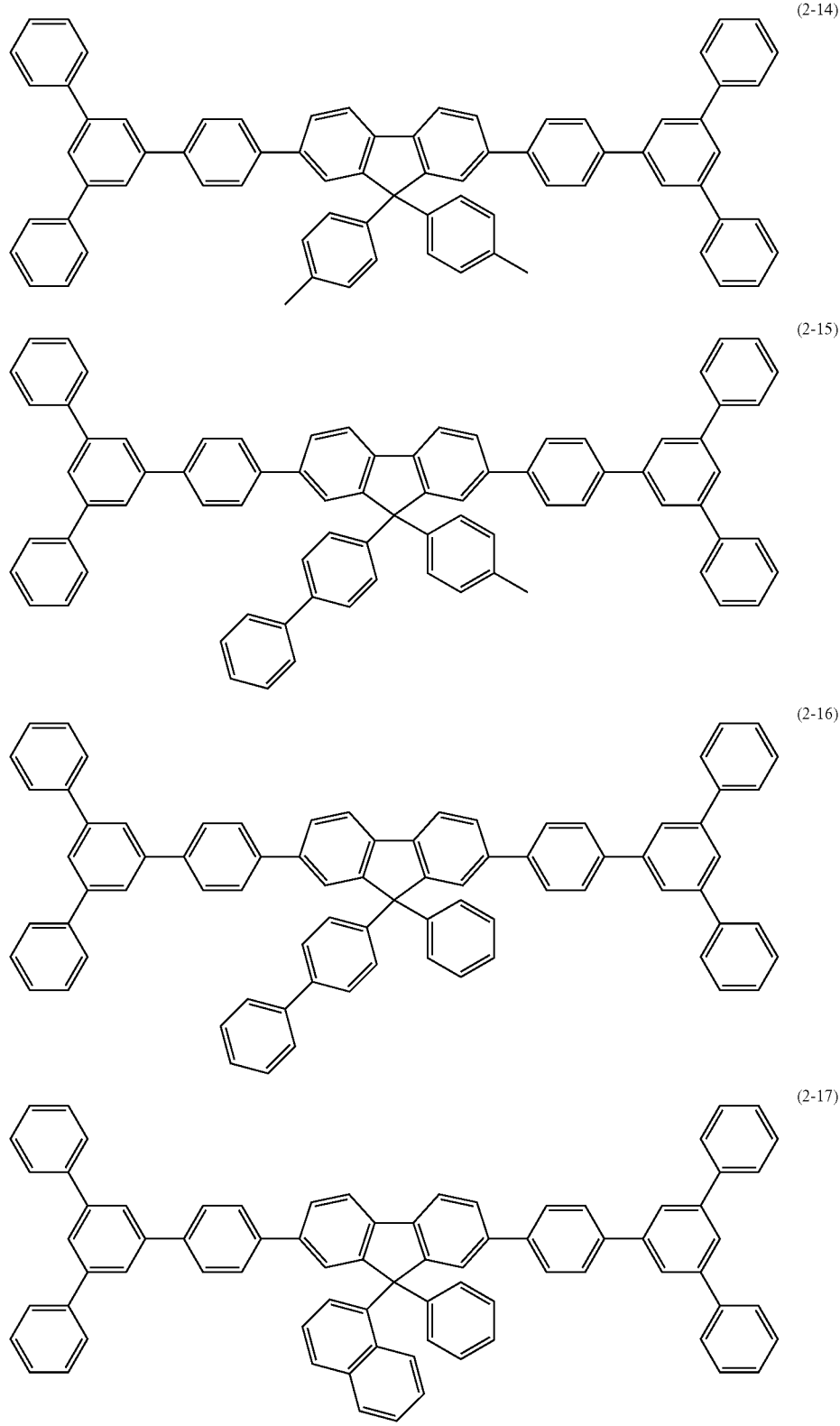
(2-14)
(2-15)
(2-16)
(2-17)

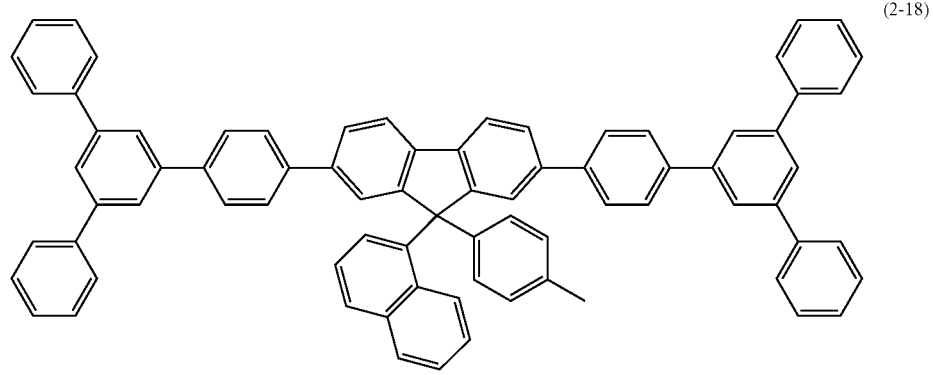
(2-18)
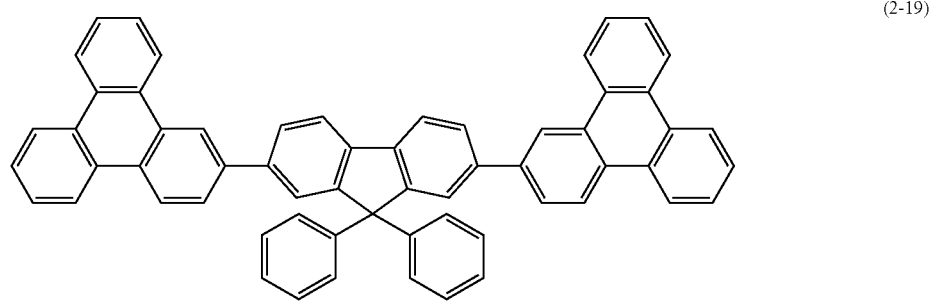
(2-19)
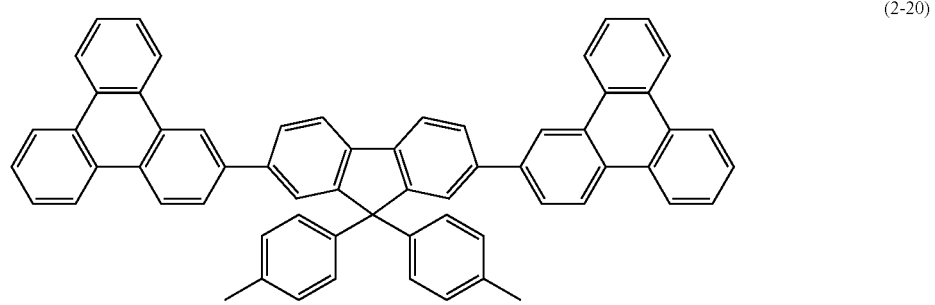
(2-20)
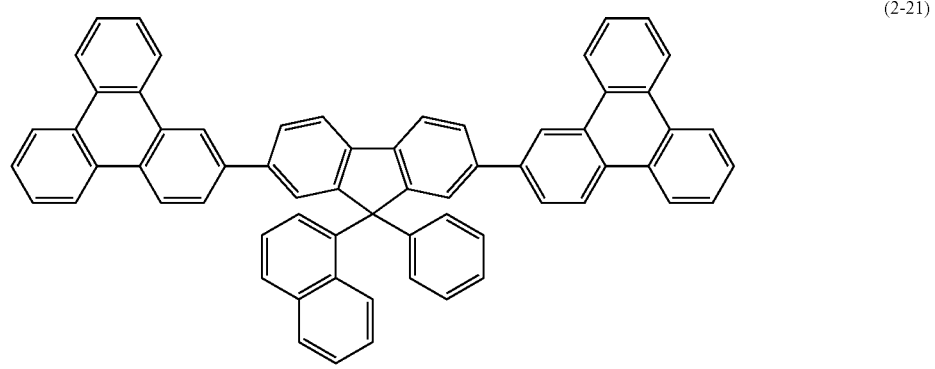
(2-21)

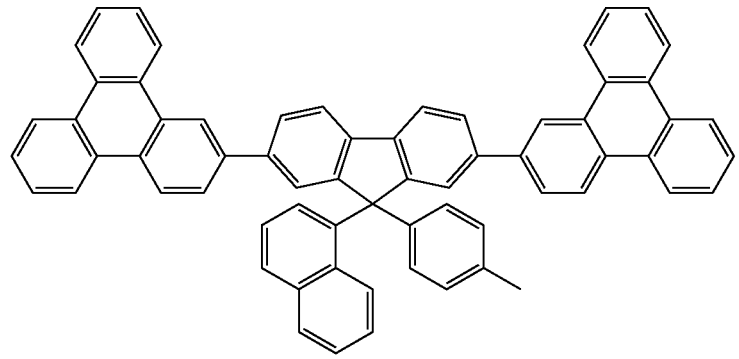
(2-22)
(2-23)
(2-24)
(2-25)

-continued (2-26)

(2-27)

(2-28)

(2-29)

(2-30)

(ii) Ar1 and Ar2 each represents a replaceable aryl group having 6 to 12 carbon atoms, and G1 and G2 each represents a replaceable amino group.
Formula (3-1) to (3-55)
(3-1)
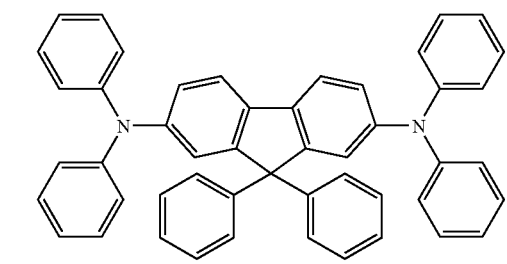
(3-2)
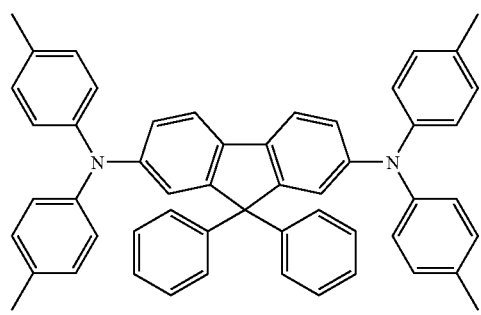
(3-3)
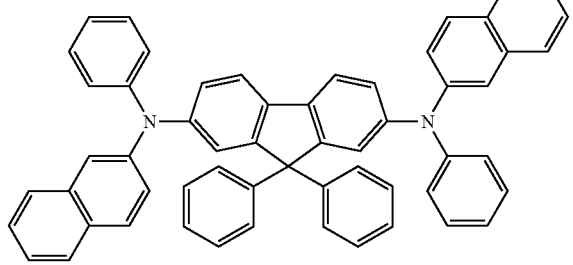
(3-4)
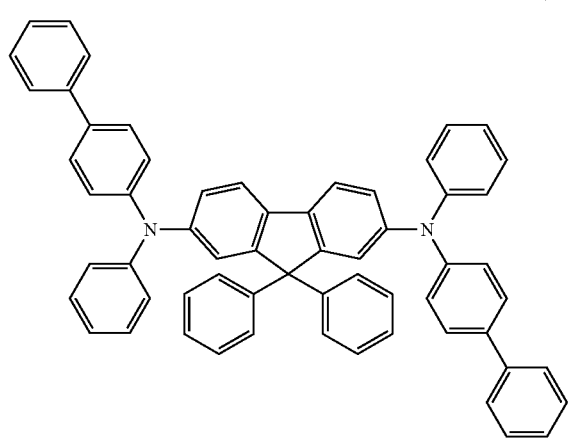
-continued
(3-5)
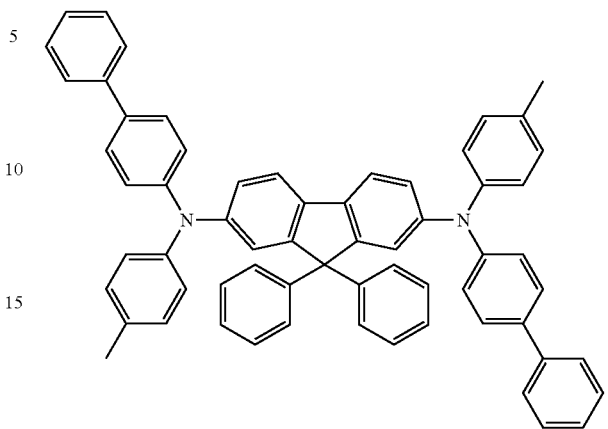
(3-6)
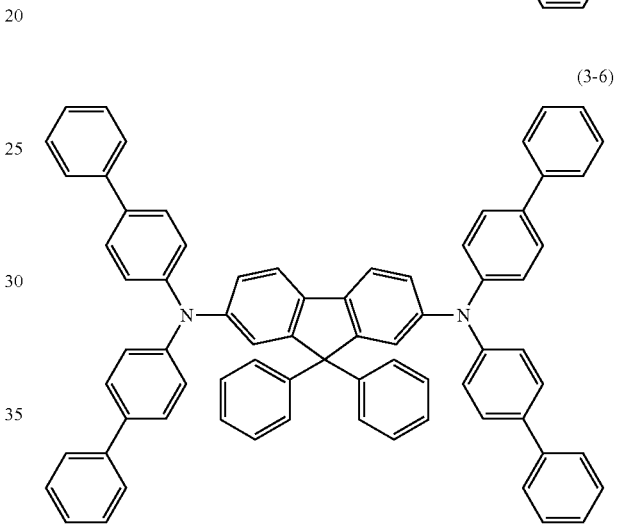
(3-7)
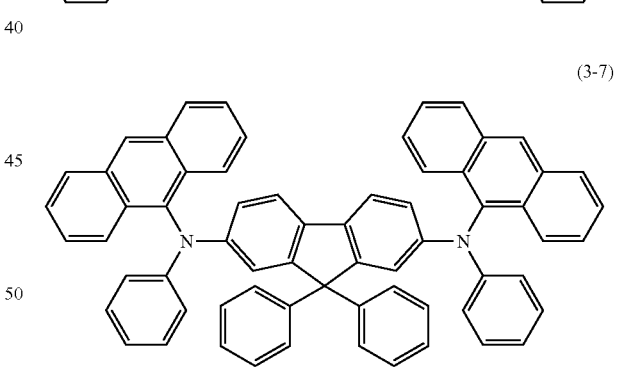
(3-8)
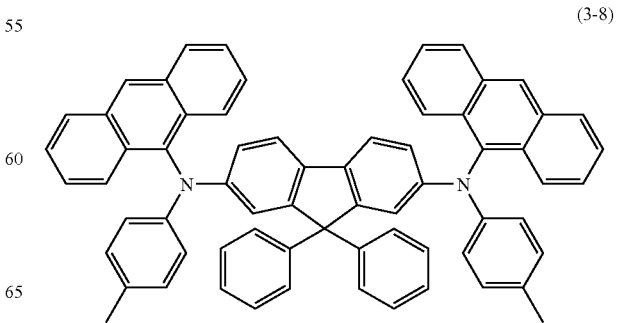

(3-9)
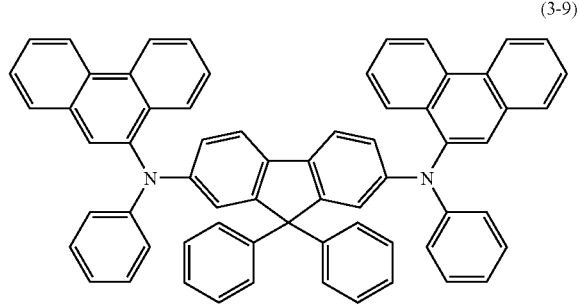
(3-10)
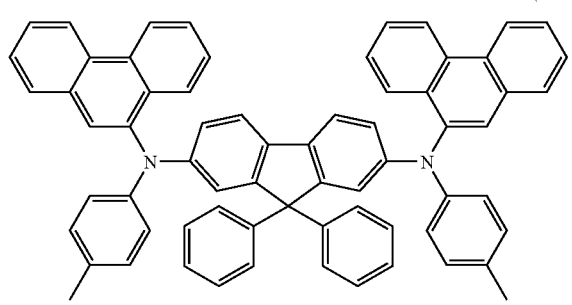
(3-11)
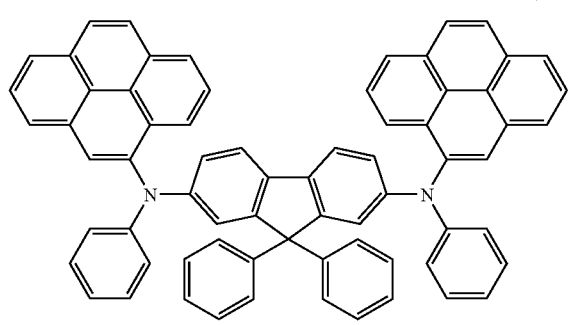
(3-12)
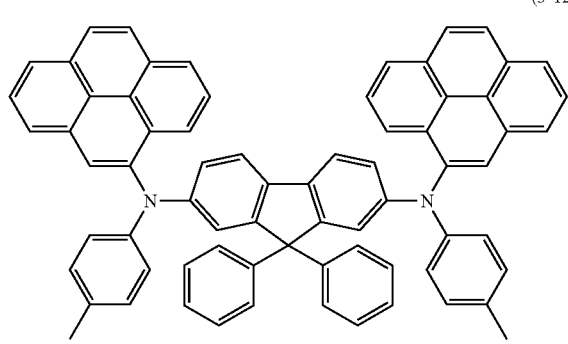
(3-13)
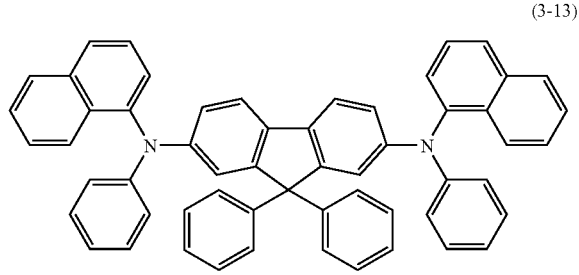
(3-14)
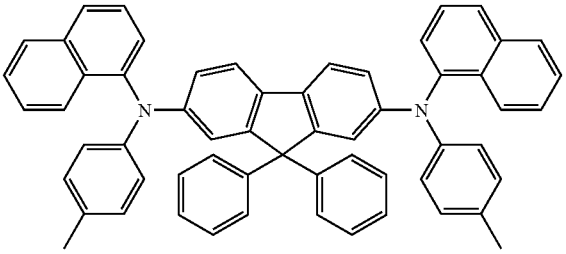
(3-15)
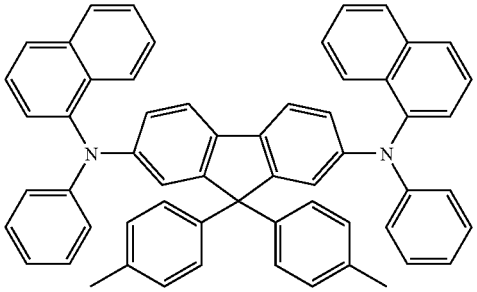
(3-16)
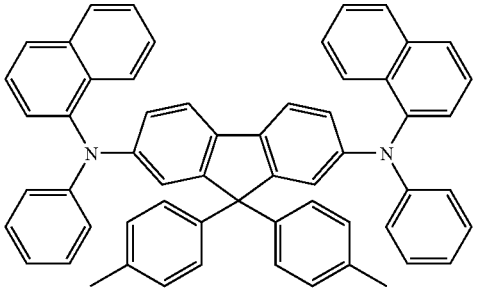
(3-17)
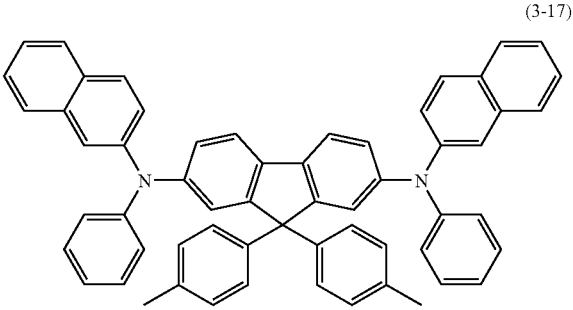
(3-18)
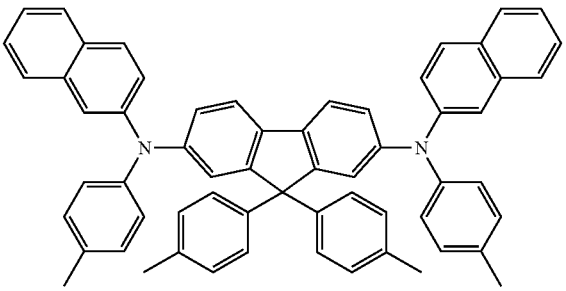

(3-19)
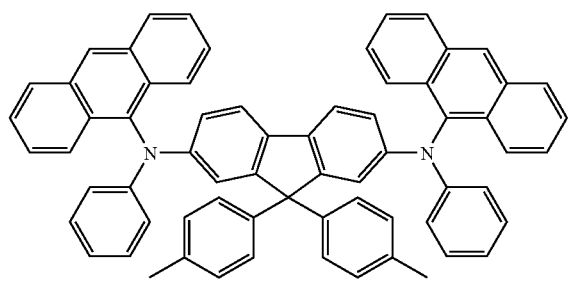
(3-20)
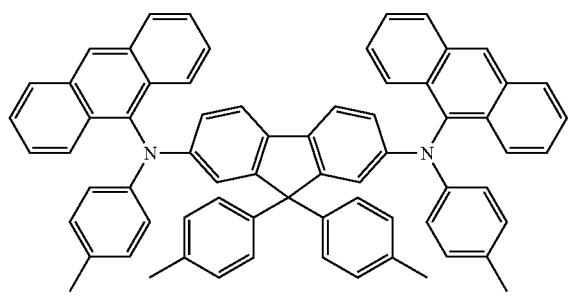
(3-21)
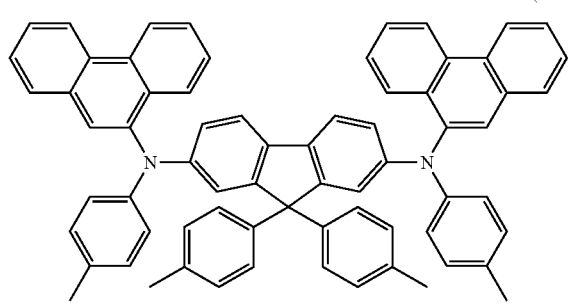
(3-22)
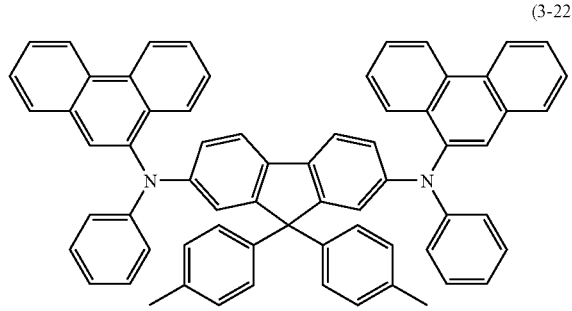
(3-23)
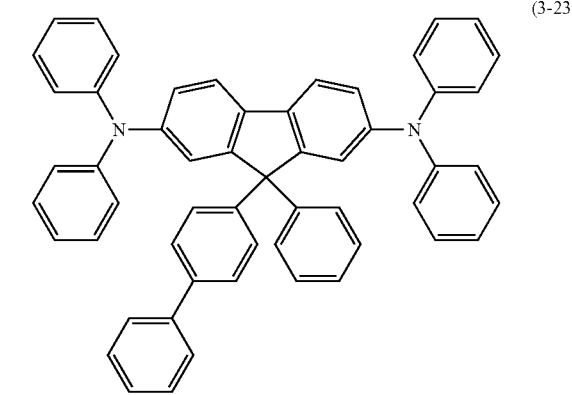
(3-24)
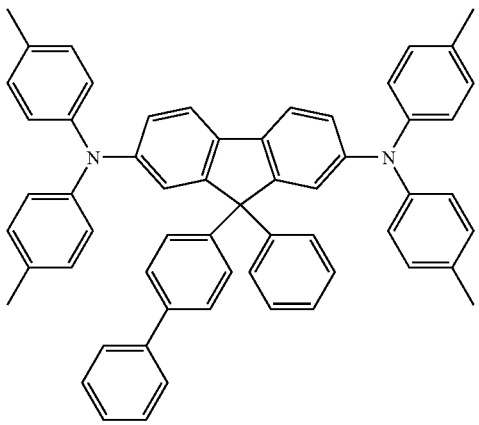
(3-25)
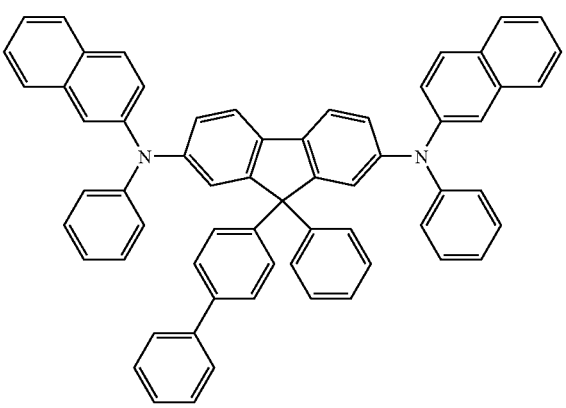
(3-26)
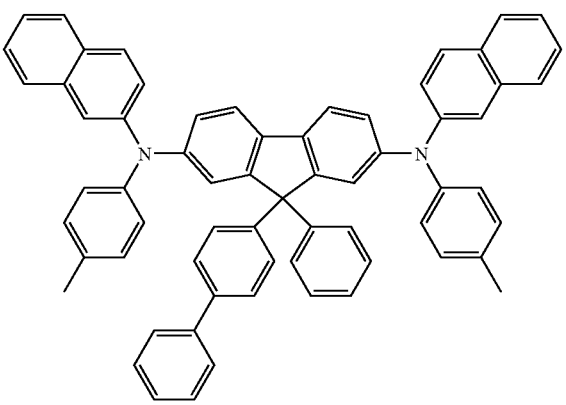
(3-27)
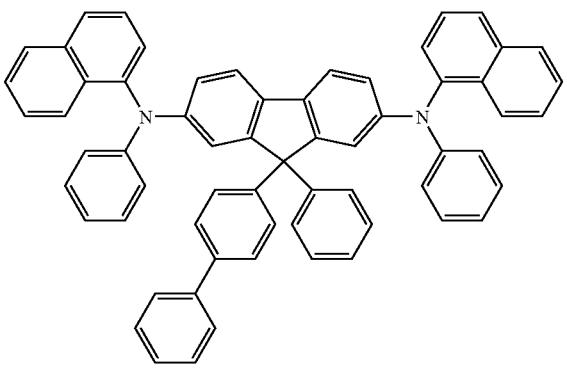

-continued
(3-28)
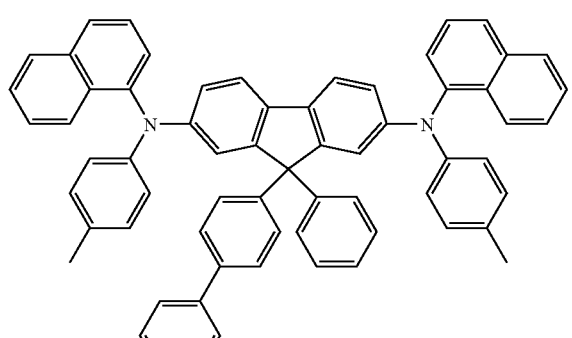
(3-29)
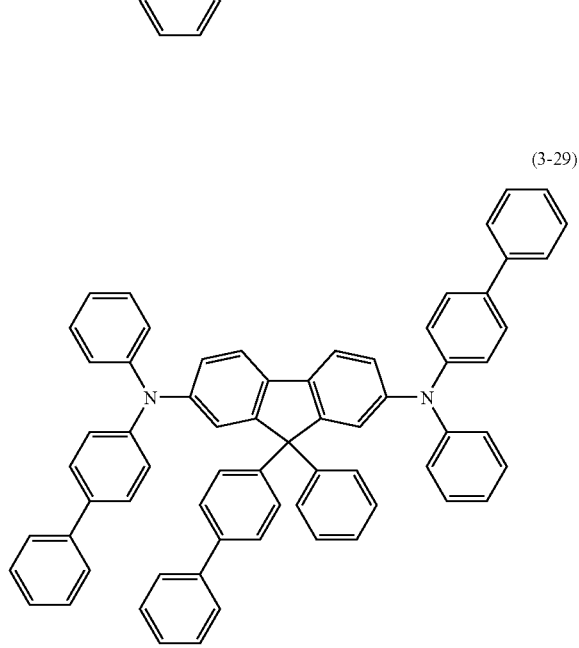
(3-30)
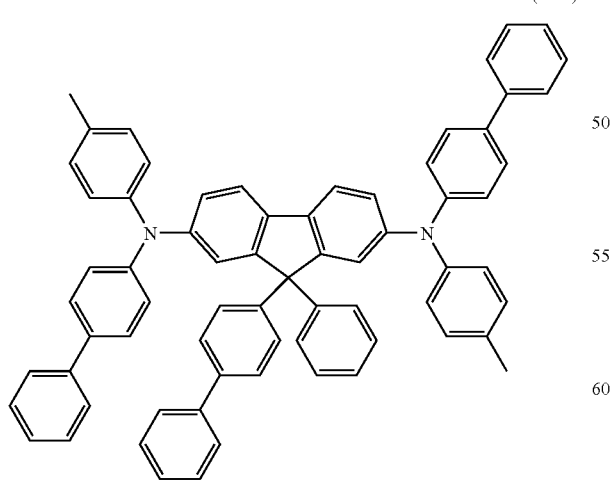
-continued
(3-31)
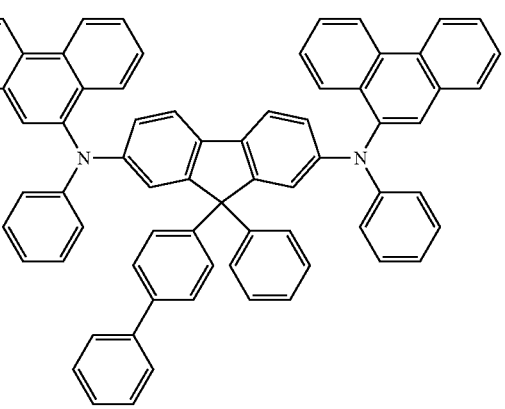
(3-32)
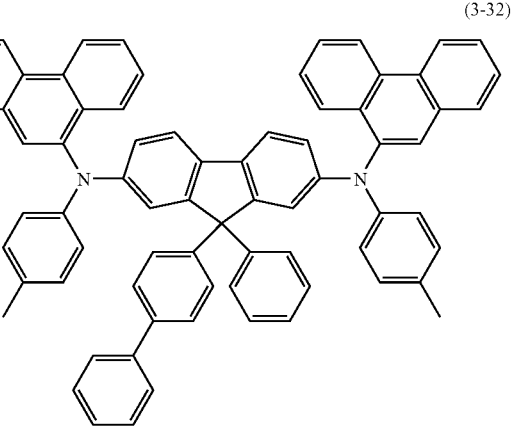
(3-33)
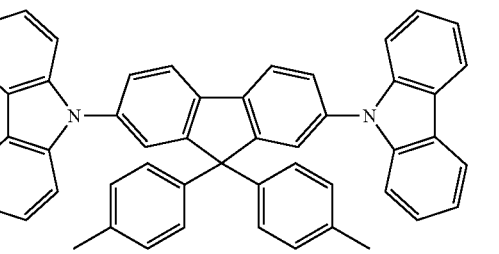
(3-34)
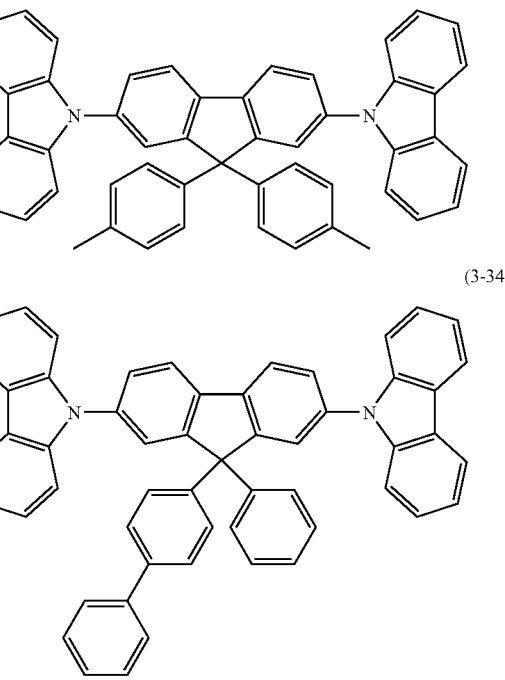

-continued
(3-35)
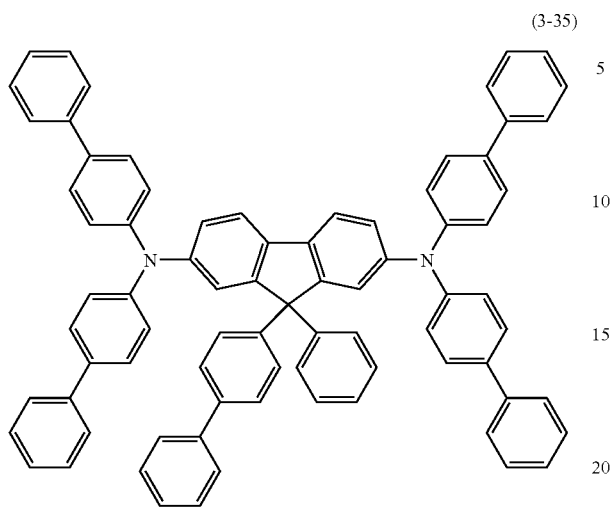
(3-36)
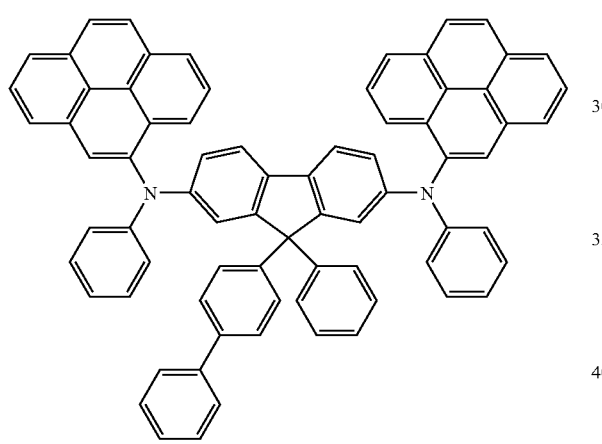
(3-37)
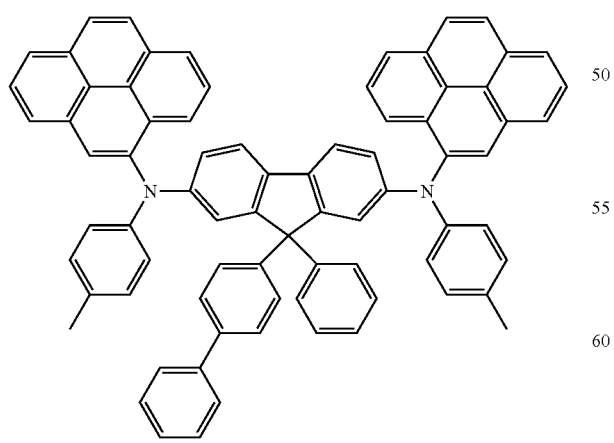
-continued
(3-38)
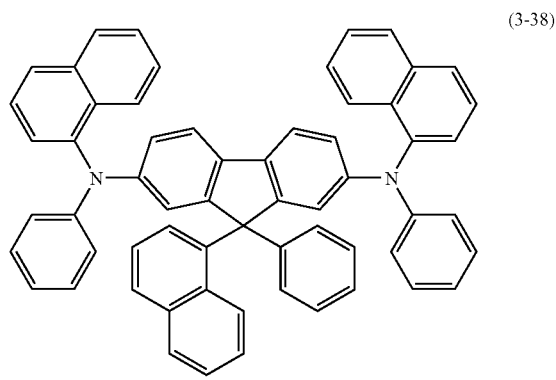
(3-39)
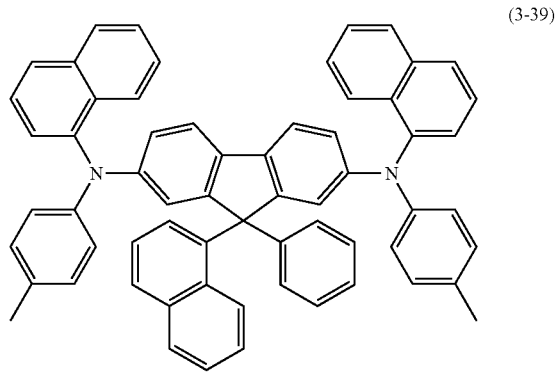
(3-40)
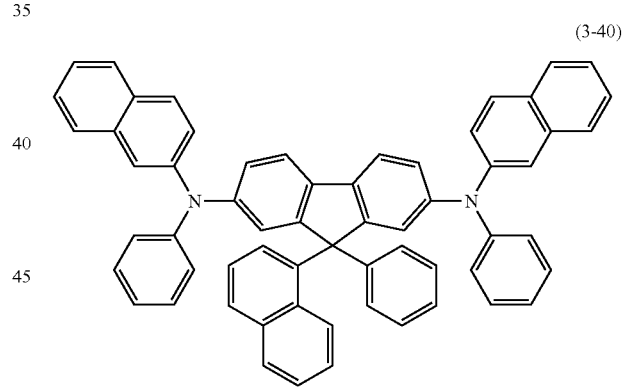
(3-41)
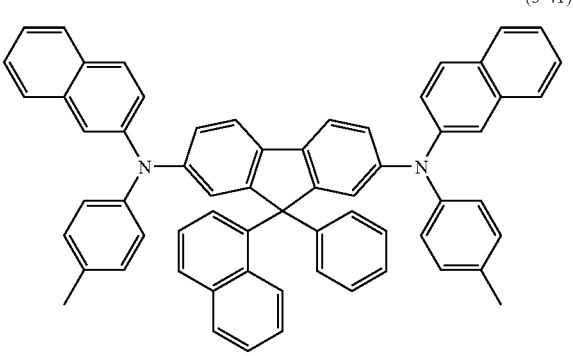

-continued
(3-42)
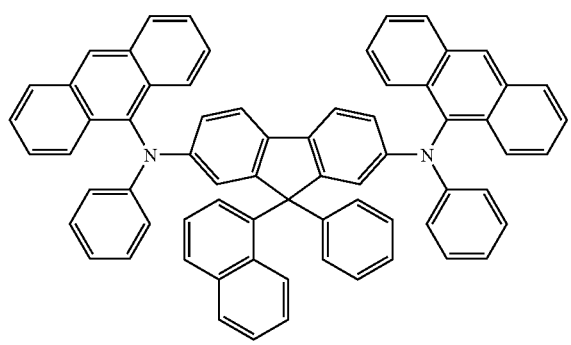
(3-45)
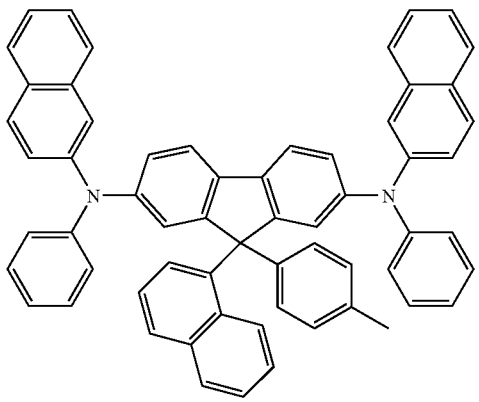
(3-43)
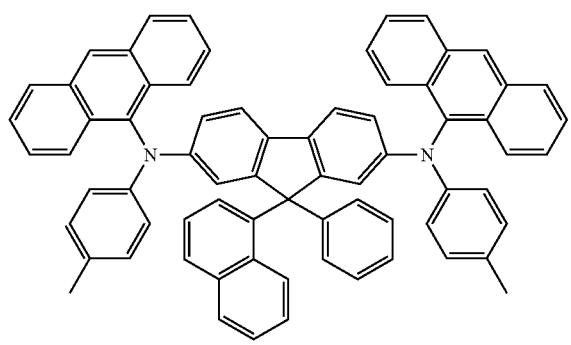
(3-46)
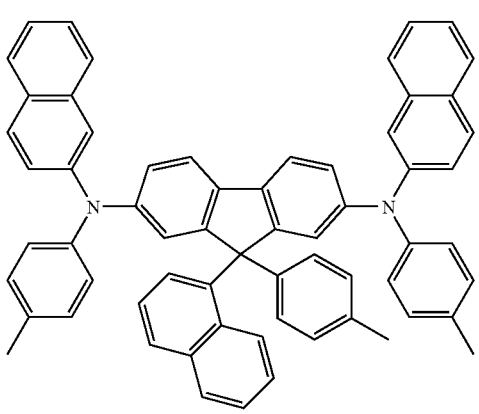
(3-43)
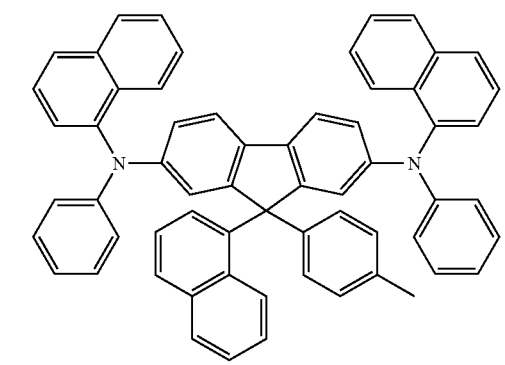
(3-47)
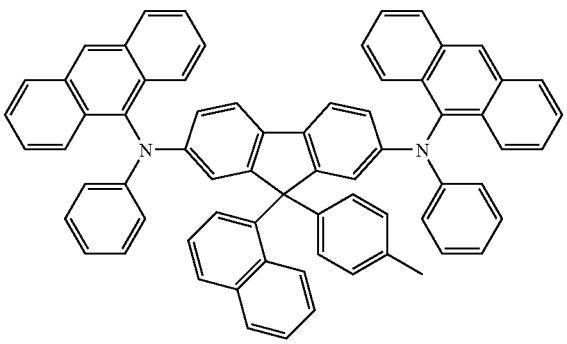
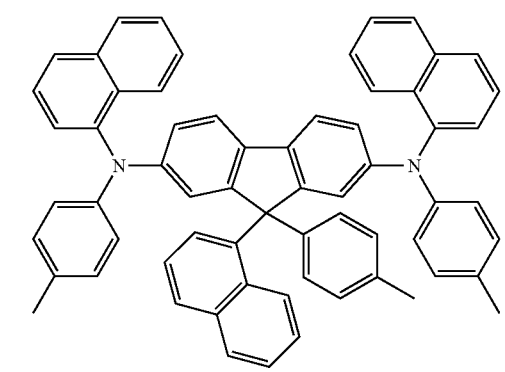
(3-48)
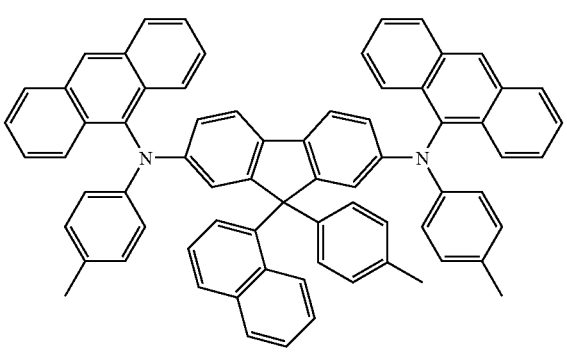

-continued
(3-49)
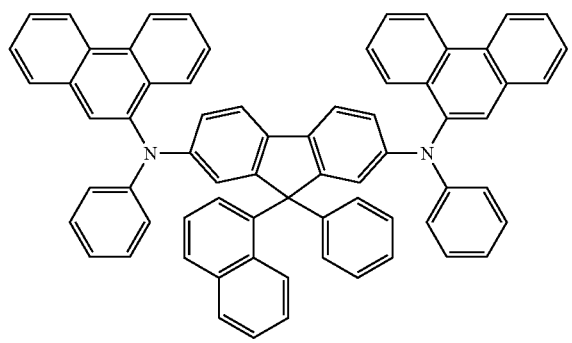
(3-50)
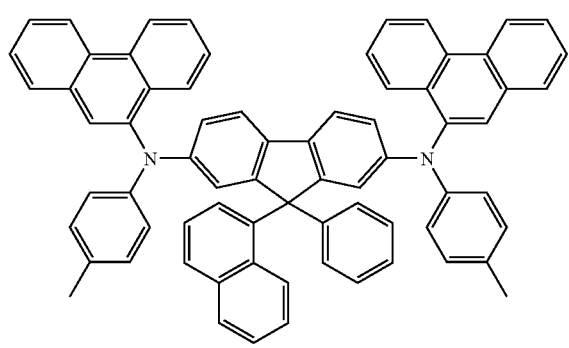
(3-51)
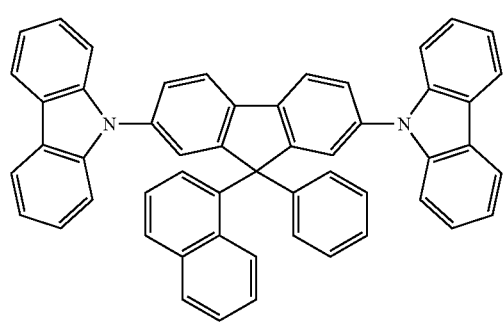
(3-52)
-continued
(3-52)
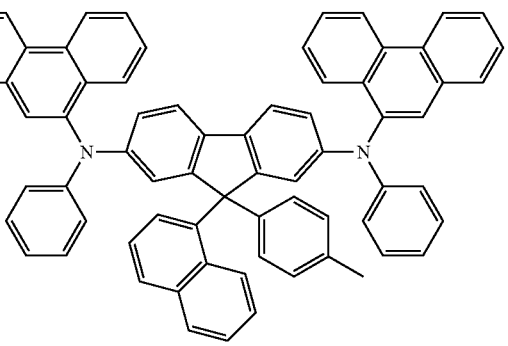
(3-53)
(3-54)
(3-55)
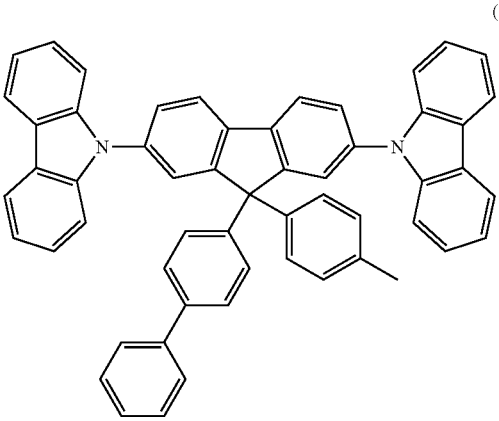

(iii) Ar1 and Ar2 each represents a replaceable aryl group having 6 to 12 carbon atoms, and G1 and G2 each represents a replaceable boron group.
Formula (4-1) to (4-16)
(4-1)
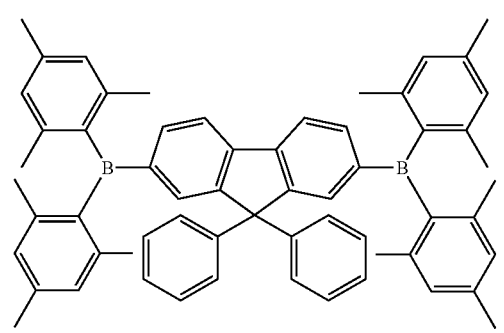
(4-2)
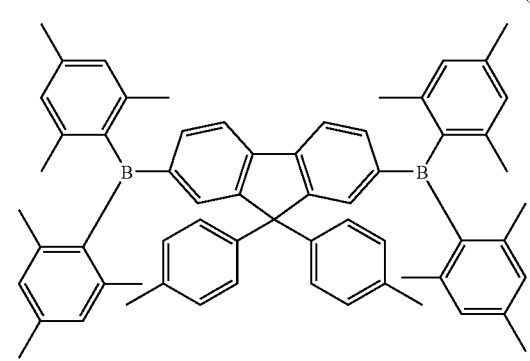
(4-3)
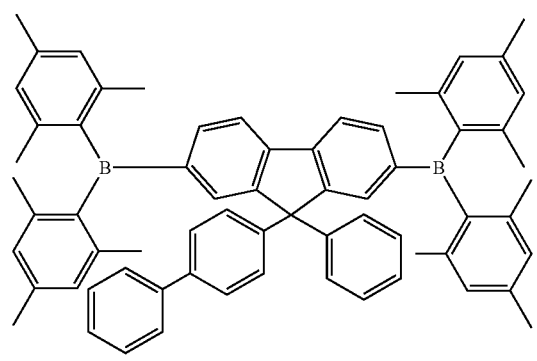
(4-4)
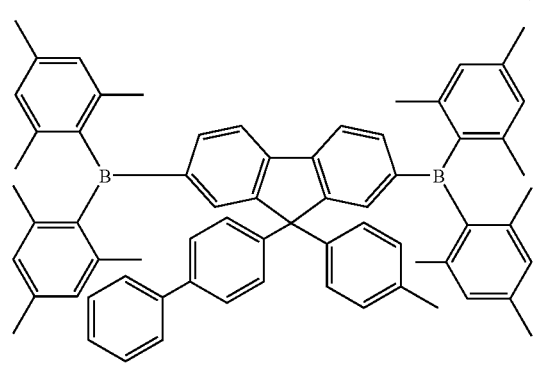
-continued
Formula (4-5)
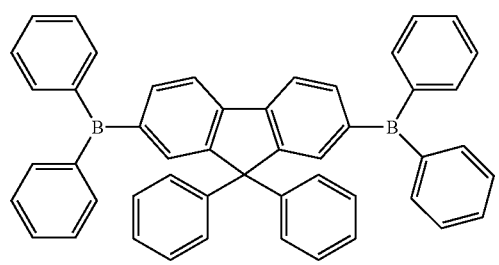
Formula (4-6)
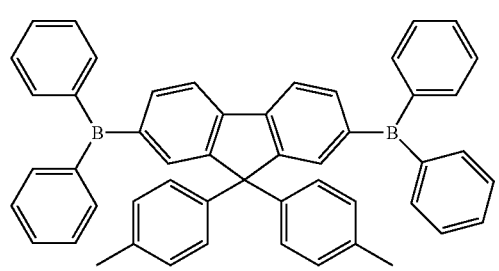
Formula (4-7)
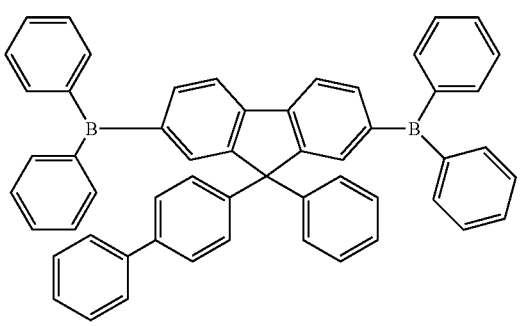
Formula (4-8)
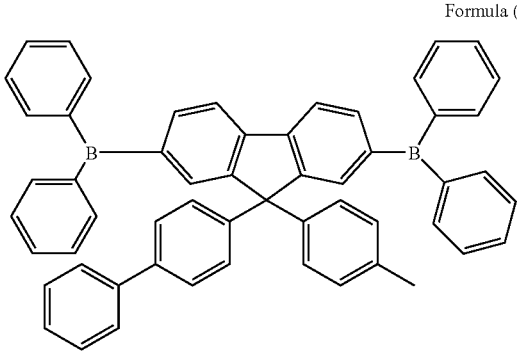
Formula (4-9)
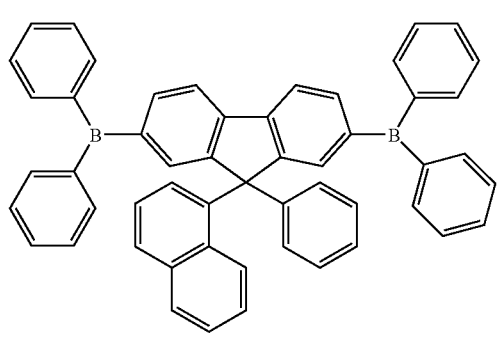

-continued
Formula (4-10)
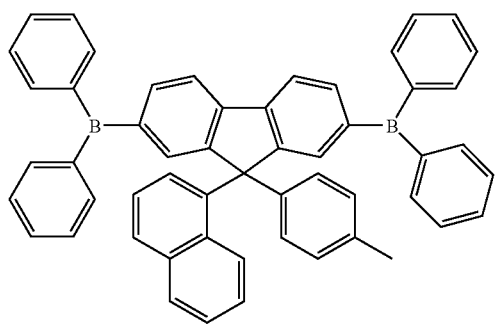
Formula (4-11)
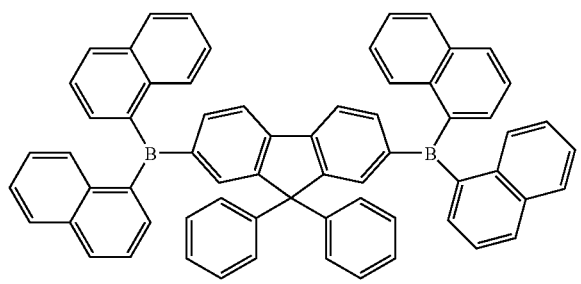
Formula (4-12)
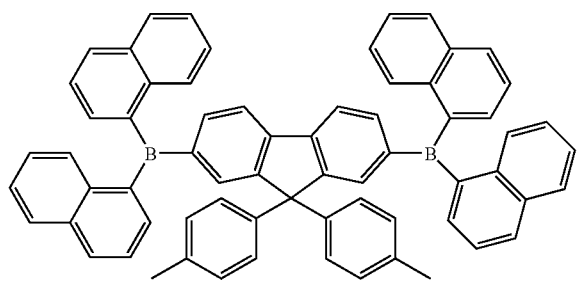
Formula (4-13)
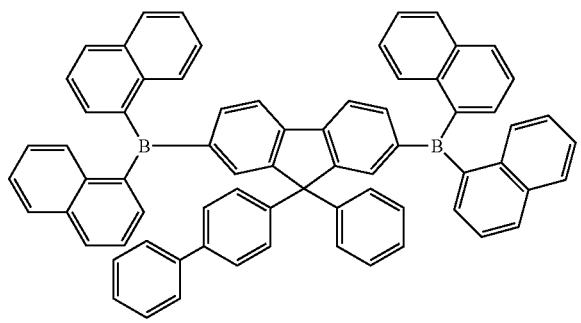
Formula (4-14)
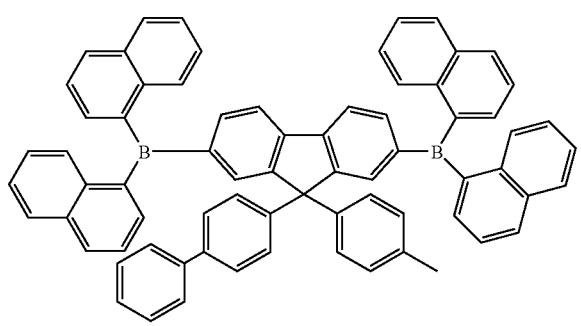
-continued
Formula (4-15)
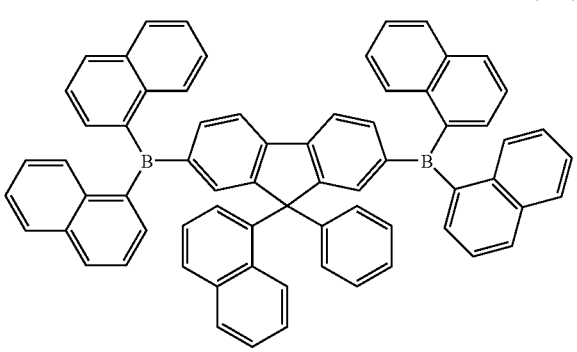
Formula (4-16)
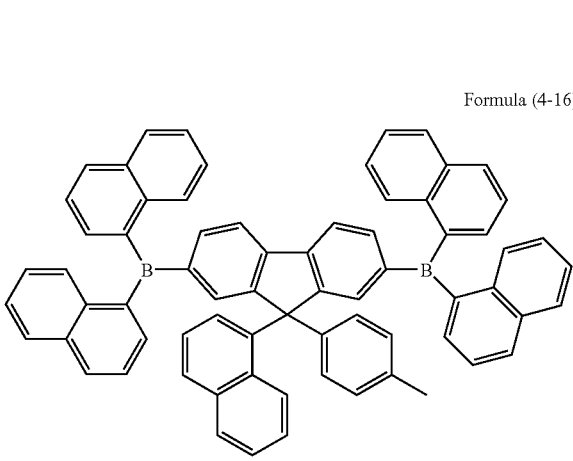
(iv) Ar1 and Ar2 each represents a replaceable aryl group having 6 to 12 carbon atoms, and G1 and G2 each represents a replaceable silyl group having 3 to 18 atoms.
Formula (5-4) to (5-6)
(5-1)
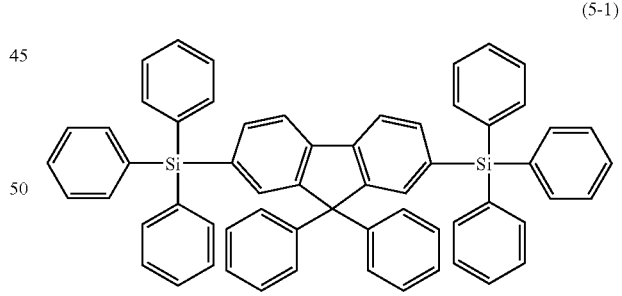
(5-2)
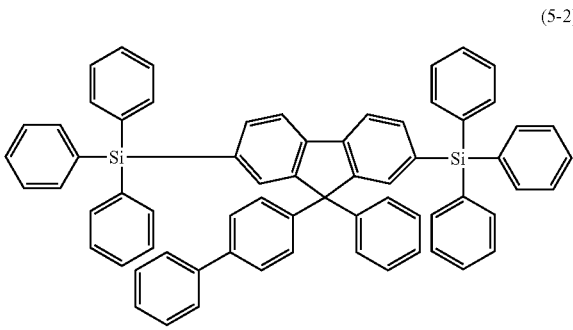

-continued (5-3)
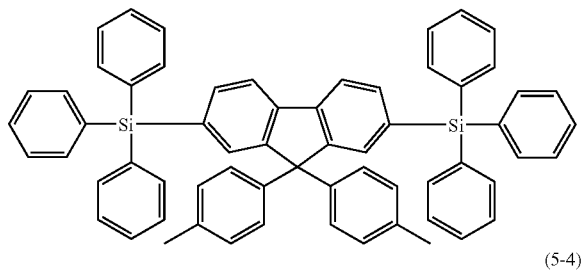

(5-4)
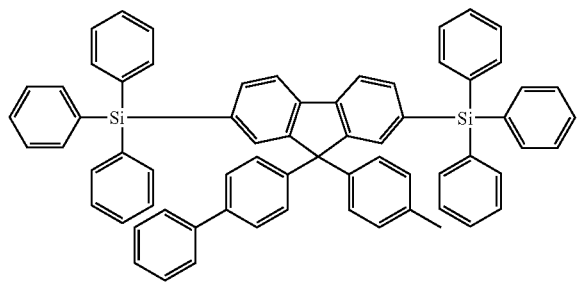

(5-5)
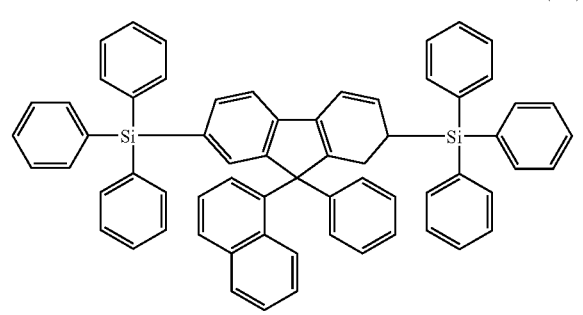

(5-6)

Preferably, n from the compounds of Formula (1) described in the embodiments above is equal to 1, in which n may also be equal to a value from 2 through 4. According to a preferred embodiment of the present invention, n equals an integer between 1 and 4. If n is greater than 4, the electrons and holes will be difficult to resonate and illuminate in the compound shown from Formula (1). Specifically, the material described above can be utilized as a hole-blocking material. If the compound from Formula (1) is utilized in the organic luminescent layer 104, a dopant is also included in the organic luminescent layer 104. Preferably, the dopant is selected from the fluorescent material consisting of at least two of Iridium (III) Bis(2-(4,6-difluorophenyl)pyridinato-N,C$^2$) picolinate, (FIr(pic)$_3$); Tris(2-phenyl pyridine) iridium(III), (Ir(ppy)$_3$); Iridium (III) Tris(2-4-totyl) pyridinato-N,C$^2$, (Ir(m-ppy)$_3$); Iridium(III) Bis(2-(2'-benzothienyl) pyridinato-N,C$^{3'}$)) (acetyl acetonate), (Ir(btp)$_2$acac); Iridium (III) Tris(2-(2'-benzothienyl) pyridinato-N,C$^{3'}$, (Ir(btp)$_3$); Bis(dibenzo [f,h] quinoxaline) iridium(III), (Ir(DBQ)$_2$acac); Platinum (II) Octaethylprophyrin, (PtOEP); Iridium(III) bis(2'-para-tol-ylpyridnato-N,C2')diethyl bis(1-pyrazoyl)borate, (Ir(tpy)$_2$(pz2BEt2)); Iridium(III)bis(2'-para-tol-ylpyridnato-N,C$^{2'}$) diphenyl bis(1-pyrazolyl)borate, (Ir(tpy)$_2$(pz2BPh2)); Bis(1-phenylisoquinoline) (acetyl acetonate) iridium(III), (Ir(piq)$_2$(acac)); Bis(2-(4'-fluorophenyl)isoquinoline) (acetyl acetonate) iridium(III), (Ir(piq-F)$_2$(acac)); Bis(5-(4'-fluorophenyl)-(3,4-benzoquinoline) (acetyl acetonate) iridium (III), (Ir(pbq-F)$_2$(acac)); Tris(2-(4'-fluorophenyl)isoquinoline) iridium(III), (Ir(piq-F)$_3$); Tris(1-phenylisoquinoline) iridium(III), (Ir(piq)$_3$); and Tris(5-(4'-fluorophenyl)-(3,4-benzoquinoline) iridium(III), (Ir(pbq-F)3). Depending on the requirement of the experiment, different combinations of dopants can be selected to produce organic luminescent devices with different wavelengths. The chemical formulae of the dopants are listed below:

FIr(pic)$_3$
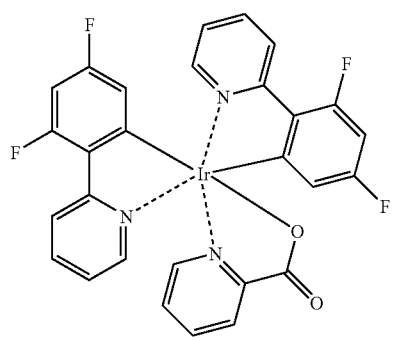

Ir(ppy)$_3$
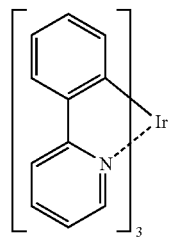

Ir(m-ppy)$_3$
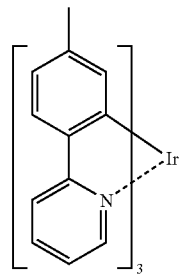

Ir(btp)$_2$acac
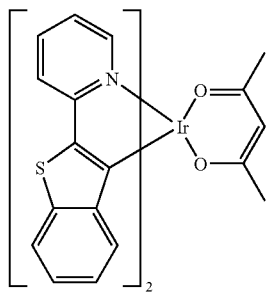

Ir(btp)₃
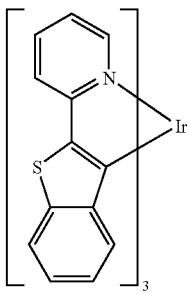
Ir(DBQ)₂acac
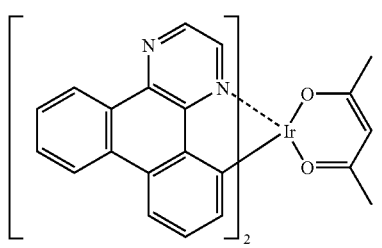
PtOEP
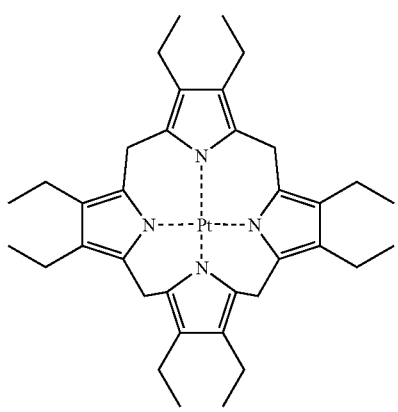
Ir(tpy)₂(pz2BEt2)
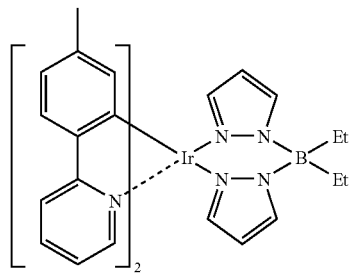
Ir(tpy)₂(pz2Bph2)
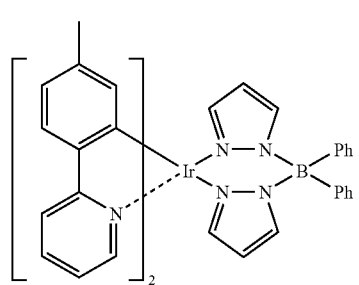
Ir(piq)₂(acac)
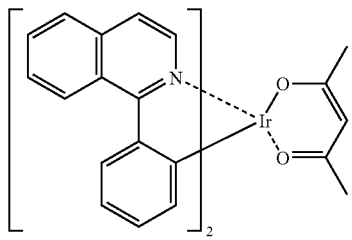
Ir(pbq-F)₂(acac)
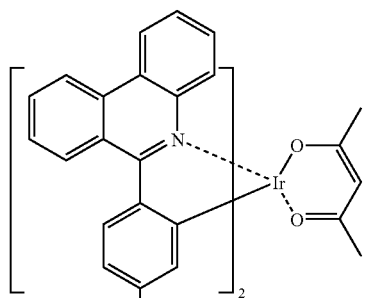
Ir(piq-F)₃
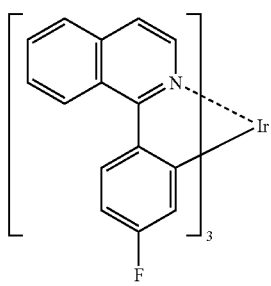
Ir(piq)₃
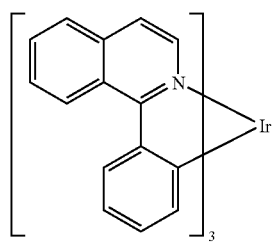
Ir(pbq)₃
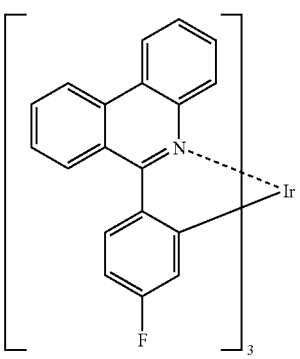

Synthesis embodiments 1 through 5 relating to the material of the present invention are described in detail below. However, the embodiments of the material are not limited thereto.

Synthesis Embodiment 1

The present embodiment involves a synthesis of the compound from Formula (2-3).

First, 1.46 grams (60 mMol) of magnesium is added into a tetrahydrofuran (THF) solution and iodide ($I_2$) in a nitrogen-rich environment. Next, 50 ml of THF mixed with 14.0 grams (60 mMol) of 4-bromobiphenyl is slowly added by means of dropper funnels to the solution provided previously, and the solution is heated to reflux for one hour thereafter. After the temperature is cooled down, the mixed solution is placed into a reaction bottle containing 3.43 grams (30 mM) of $B(OME_3)$ and 30 grams of THF and cooled down at a temperature of −78° C. Next, a grignard agent is slowly added into the reaction bottle, and after reacting for five hours, the solution is cooled down and stirred continuously. Subsequently, a rotary concentrator is utilized to remove the solvent from within the solution, and after adding ethylene glycol and toluene into the solution, the solution is heated to reflux. After extracting the solvent from the toluene layer, 9.1 grams of 2-biphenyl-4-yl-[1,3,2]dioxaborolane is obtained, in which the yield of the extraction is approximately 82%.

Next, a mixture containing 0.57 grams (1 mM) of 9-biphenyl-4-yl-2,7-dibromo-9-p-toyl-9H-fluorene, 0.54 grams (24 mM) of 2-biphenyl-4-yl-[1,3,2]dioxaborolane, 2 ml of 2M $K_2CO_3$, 3.4 grams (0.03 mM) or $Pd(PPh_3)_4$, and 0.6 ml of $P(tBu_3)$ is obtained, and 2 ml of toluene is added into the mixture and heated for at least 12 hours. After cooling down the mixture, a chloroform extraction is utilized to remove the solvent, and the organic layer is washed by water and dried by magnesium sulfate. A rotary concentrator is utilized to remove the solvent and obtain a white solid thereafter. Next, a column purification is performed on the white solid, such as separated by 20% chloroform and hexane, to obtain the chemical formula (2-3). The chemical reaction of the Formula (2-3) is shown below.

Synthesis Embodiment 2

The present embodiment involves a synthesis of the compound from Formula (3-55).

First, 0.91 grams (3.75 mM) of magnesium is added into a tetrahydrofuran (THF) solution and iodide ($I_2$) in a nitrogen-rich environment. Next, 35 ml of THF mixed with 8.7 grams (37.5 mM) of 4-bromobiphenyl is slowly added by means of dropper funnels to the solution provided previously, and the solution is heated to reflux for one hour. Next, 60 ml of THF mixed with 8.4 grams (25 mM) of 2,7-dibromo-fluorenone is added into the previous solution, and after a grignard agent is added, the solution is heated to reflux. Next, water is added to the reacting mixture, a chloroform extraction is performed, and the organic layer is washed two times by water and dried by magnesium sulfate. Next, a rotary concentrator is utilized to remove the solvent, and ethyl acetate is utilized to initiate a recrystallization reaction and produce 9-biphenyl-4-2,7-dibromo-9H-fluorene-9-ol.

Next, 9-biphenyl-4-2,7-dibromo-9H-fluorene-9-ol is dissolved in toluene, and a toluene solvent containing concentrated sulfuric acid is added into the solution and react for one hour. After the solution is cooled down, sodium carbonate is added into the solution. Next, a chloroform extraction is performed, and the organic layer is washed two times by water and dried by magnesium sulfate. Next, the rotary concentrator is utilized to remove the solvent, and chloroform and methanol are utilized to initiate a recrystallization reaction and produce 9-biphenyl-4-yl-2,7-dibromo-9-p-toyl-9H-fluorene.

Next, 1.5 grams (9 mM) of carbazole, 1.7 grams (3 mM) of 9-biphenyl-4-yl-2,7-dibromo-9-p-toyl-9H-fluorene, 0.8 grams (8.3 mM) of sodium tert-butoxide, and 1.3 grams of $Pd(OAc)_2$ is dissolved in 30 ml of xylene, and 2 ml (0.24 mM) of tri-tert-butylphosphine is added into the solution. Next, nitrogen gas is injected and the previous solution is heated to reflux for 24 hours. After the solution is cooled down, crystals are precipitated by adding ethanol, and the product is filter thereafter. Next, acetone is added to initiate a recrystallization reaction and obtain 1.86 grams of white crystals. Subsequently, a column purification is performed on the white crystals to obtain the compound shown in Formula (3-55). The chemical reaction of Formula (3-55) is shown below.

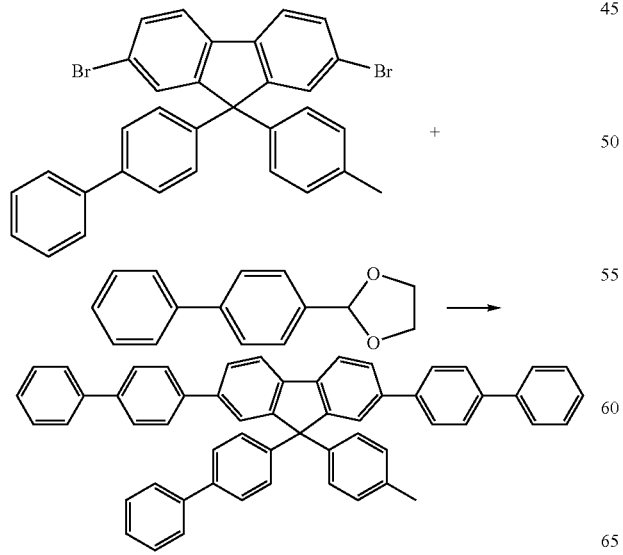

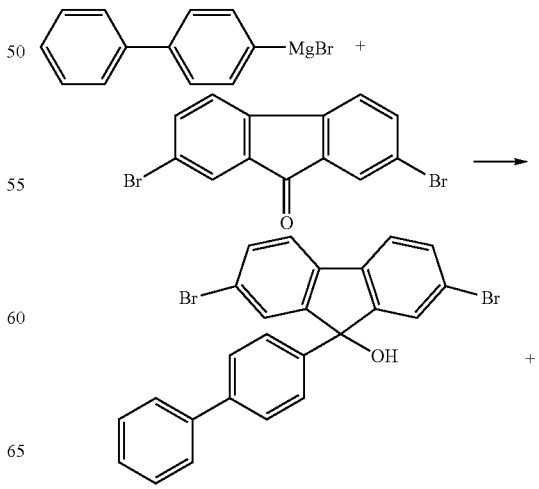

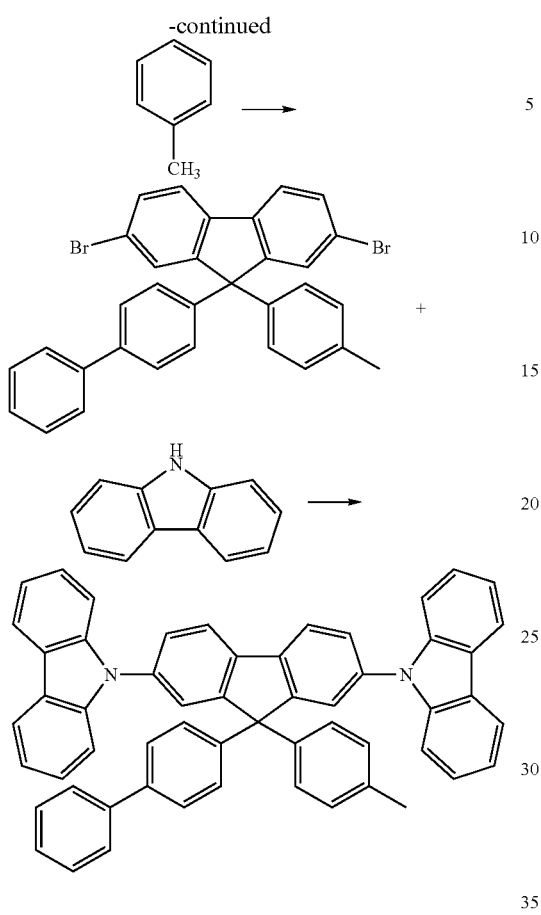

Synthesis Embodiment 3

The present embodiment involves a synthesis of the compound from Formula (3-54).

First, 0.91 grams (3.75 mM) of magnesium is added into a tetrahydrofuran (THF) solution and iodide (I$_2$) in a nitrogen-rich environment. Next, 35 ml of THF mixed with 5.9 grams (37.5 mM) of 4-bromobiphenyl is slowly added by means of dropper funnels to the solution provided previously, and the solution is heated to reflux for one hour. Next, 60 ml of THF mixed with 8.4 grams (25 mM) of 2,7-dibromo-fluorenone is added into the previous solution, and after a grignard agent is added, the solution is heated to reflux. Next, water is added to the reacting mixture, a chloroform extraction is performed, and the organic layer is washed two times by water and dried by magnesium sulfate. Next, a rotary concentrator is utilized to remove the solvent, and ethyl acetate is utilized to initiate a recrystallization reaction and produce 2,7-dibromo-9-phenyl-9H-fluorene-9-ol.

Next, 2,7-dibromo-9-phenyl-9H-fluorene-9-ol is dissolved in benzene, and benzene containing concentrated sulfuric acid is added into the solution and react for one hour. After the solution is cooled down, sodium carbonate is added into the solution. Next, a chloroform extraction is performed, and the organic layer is washed two times by water and dried by magnesium sulfate. Next, the rotary concentrator is utilized to remove the solvent, then chloroform and methanol are utilized to initiate a recrystallization reaction and produce 2,7-di bromo-9,9-diphenylfluorene.

Next, 1.5 grams (9 mM) of carbazole, 1.4 grams (3 mM) of 2,7-dibromo-9,9-diphenylfluorene, 0.8 grams (8.3 mM) of sodium tert-butoxide, and 1.3 grams of Pd(OAc)$_2$ is dissolved in 30 ml of xylene, and 2 ml (0.24 mM) of tri-tert-butylphosphine is added into the solution. Next, nitrogen gas is injected and the previous solution is heated to reflux for 24 hours. After the solution is cooled down, crystals are precipitated by adding ethanol, and the product is filter thereafter. Next, acetone is added to initiate a recrystallization reaction and obtain 1.42 grams of white crystals. Subsequently, a column purification is performed on the white crystals to obtain the compound shown in Formula (3-54). The chemical reaction of Formula (3-54) is shown below.

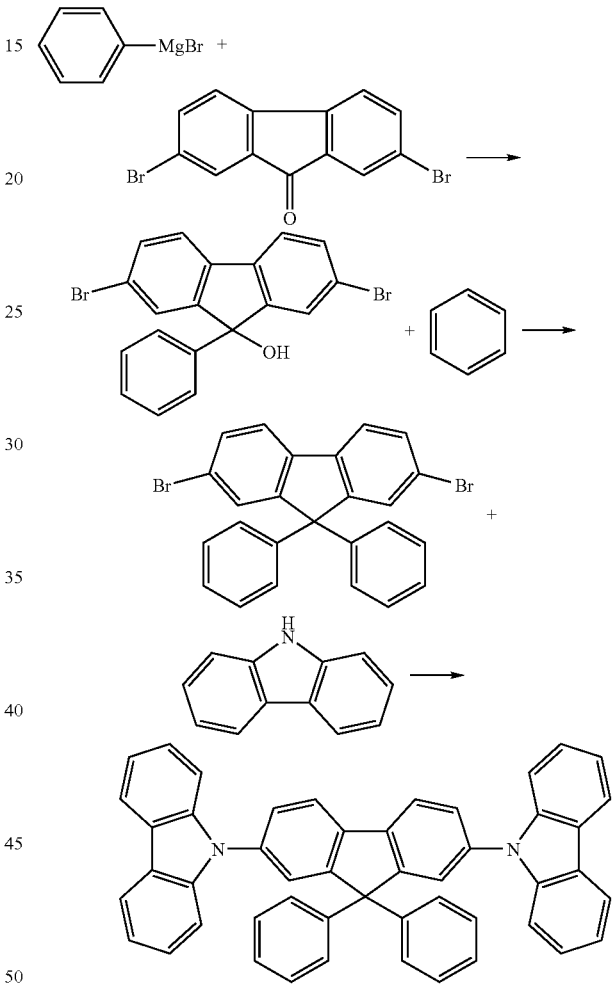

Synthesis Embodiment 4

The present embodiment involves a synthesis of the compound 2,7-bis-[bis-(2,4,6-trimethyl-phenyl)-boranyl]-9,9-diphenyl-9H-fluorene from Formula (4-1).

First, under a nitrogen-rich environment, 4.76 grams (0.01 M) of 2,7-dibromo-9,9-diphenylfluorene is stirred and dissolved in 60 ml of anhydrous THF, and the solution is cooled down to −78° C. Next, 12.5 ml of n-butyllithium (1.6 M in hexane) is slowly dropped into a reaction bottle, and to prevent the temperature of the solution from increasing above −68° C., the solution is stirred for one hour at a temperature of −78° C. Next, 5.6 grams (0.021 ml) of dimesitybom fluoride is dissolved in 30 grams of anhydrous THF, in which the solution is slowly dropped into the reaction solution thereafter. After the solution is cooled down, the temperature of the solution is increased to room temperature naturally (i.e., without utilizing external heating/cooling sources) and stirred for at least 12 hours. Subsequently, water is added to initiate a quenching effect, and 100 ml of dichloromethane is added to induce a separation of organic layers. After two extractions are conducted, magnesium sulfate is added to remove water of the organic solution. Next, the solution is concentrated and solvents are removed, and ethanol is added to precipitate and obtain white crystals. After the white crystals are filtered and dried by vacuum, white solids are obtained. Next, a vacuum purification is performed on 2 grams of white solids to obtain 1.1 grams of white crystals, in which the white crystals are the compounds from Formula (4-1). The chemical reaction of the Formula (4-1) is shown below.

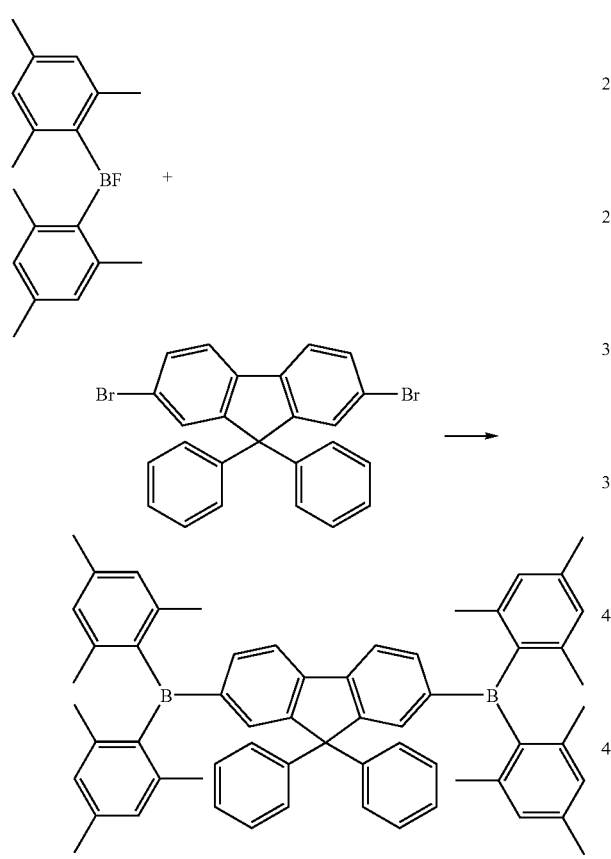

Synthesis Embodiment 5

The present embodiment involves a synthesis of the compound 9-9-diphenyl-2,7-bis-triphenylsilanyl-9H-fluorene from Formula (5-1).

First, under a nitrogen-rich environment, 4.76 grams (0.01 M) of 2,7-dibromo-9,9-diphenylfluorene is stirred and dissolved in 60 ml of anhydrous THF, and the solution is cooled down to −78° C. Next, 12.5 ml of n-butyllithium (1.6 M in hexane) is slowly dropped into a reaction bottle, and to prevent the temperature of the solution from increasing above −68° C., the solution is stirred for one hour at a temperature of −78° C. Next, 6.2 grams (0.021 ml) of chlorotriphenylsilane is dissolved in 30 grams of anhydrous THF, in which the solution is slowly dropped into the reaction solution thereafter. After the solution is cooled down, the temperature of the solution is increased to room temperature naturally and stirred for at least 12 hours. Subsequently, water is added to initiate a quenching effect, and 100 ml of dichloromethane is added to induce a separation of organic layers. After two extractions are conducted, magnesium sulfate is added to remove water of the organic solution. Next, the solution is concentrated and solvents are removed, and ethanol is added to precipitate and obtain white crystals. After the white crystals are filtered and dried by vacuum, white solids are obtained. Next, a vacuum purification is performed on 2 grams of white solids to obtain 1.2 grams of white crystals, in which the white crystals are 9-9-diphenyl-2,7-bis-triphenylsilanyl-9H-fluorene. The chemical reaction of the Formula (5-1) is shown below.

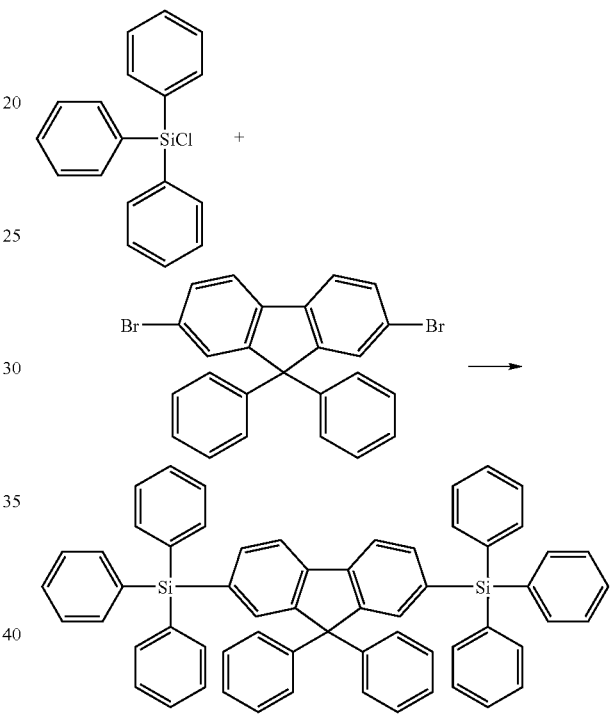

Comparative Example

The comparative group discloses a method for fabricating an organic luminescent device having a six layer organic structure. As shown in FIG. 6, a glass substrate 100 having a dimension of 45 mm×45 mm is first provided. Next, an indium tin oxide (ITO) layer having a thickness of 50 to 200 nm is coated on the glass substrate 100. Next, a photolithography and etching process is performed to form the indium tin oxide layer into a plurality of luminescent patterns. Each of the luminescent patterns has a dimension of 3 mm×3 mm, in which the patterns are utilized as an anode 102. Next, a vacuum evaporation process is performed at a vacuum degree of $10^{-6}$ Pa to coat a hole injection layer 112a of 50 nm on the surface of the anode 102, in which the hole injection layer 112a is composed of 4,4',4"-Tris(N-(2-naphthyl)-N-phenyl-amino)-triphenylamine (2-NTNATA). Next, a vacuum evaporation process is performed to coat a hole transport layer 112 of 20 nm on the surface of the hole injection layer 112a, in which the hole transport layer 112 is composed of N4,N4'-Di-naphthalen-1-yl-N4,N4'-diphenyl-biphenyl-4,4'-diamine (NPB).

Next, a material of CBP is placed on an evaporation dish with Ir(btp)$_2$acac, in which the ratio between CBP and Ir(btp)$_2$acac is 10:1. The evaporation process is performed at a rate of 0.2 nm/sec to form an organic luminescent layer 104 of 30 nm on the hole transport layer 112, in which the dopant within the organic luminescent layer 104 is Ir(btp)$_2$acac.

Next, a hole-blocking layer 114 of 10 nm is coated on the organic luminescent layer 104, in which the hole-blocking layer 114 is composed of 2,9-dimethyl-4,7-diphenyl-1,10-phenanthroline (BCP). The hole-blocking layer 114 can also be composed of the material from Formula (1), thereby retaining the holes in the organic luminescent layer 104 and improving the transformation efficiency for illumination of the device.

Next, an AlQ$_3$ layer is coated on the hole-blocking layer 114, in which the AlQ$_3$ layer is utilized as the electron transport layer 110. The thickness of the electron transport layer 110 is 30 nm, and the evaporation process performed is maintained at 0.2 nm/sec. Next, a lithium fluoride of 0.5 nm is coated on the electron transport layer 110, in which the lithium fluoride is utilized as the electron injection layer 110a.

Subsequently, an aluminum layer of 120 nm, functions as the cathode 106, is formed on the electron injection layer 110a to complete the fabrication of the electroluminescent device.

Preferably, the present invention is able to apply the fluorene compound shown in Formula (1) not only in the organic luminescent layer of the electroluminescent device, but also in the hole-blocking layer, as shown in the experiments B1, B2, and B3 below. Since the fluorene compound is thermally and chemically stable, the material is suitable to be utilized as the host material of the luminescent layer of the electroluminescent device, as described in the experiments B3, H1, H2, H3, and H4 below. Additionally, the fluorene compound of the present invention is able to form uniform and un-crystallized films, thereby improving the problem of the conventional electroluminescent device.

In contrast to the conventional luminescent material described above of utilizing CBP, examples utilizing compound from Formula (2-3), (3-54), and (4-1) are performed according to the following experiments.

Experiment B1 and B2

Experiments B1 and B2 disclose a method for fabricating an organic luminescent device having a six layer organic structure. Similar to the comparative example, a glass substrate 100 having a dimension of 45 mm×45 mm is first provided. Next, an indium tin oxide (ITO) layer having a thickness of 50 to 200 nm is coated on the glass substrate 100. Next, a photolithography and etching process is performed to form the indium tin oxide layer into a plurality of luminescent patterns. Each of the luminescent patterns has a dimension of 3 mm×3 mm, in which the patterns are utilized as an anode 102. Next, a vacuum evaporation process is performed at a vacuum degree of $10^{-6}$ Pa to coat a hole injection layer 112a of 50 nm on the surface of the anode 102, in which the hole injection layer 112a is composed of 4,4',4"-Tris(N-(2-naphthyl)-N-phenyl-amino)-triphenylamine (2-NTNATA). Next, a vacuum evaporation process is performed to coat a hole transport layer 112 of 20 nm on the surface of the hole injection layer 112a, in which the hole transport layer 112 is composed of N4,N4'-Di-naphthalen-1-yl-N4,N4'-diphenyl-biphenyl-4,4'-diamine (NPB).

Next, a material of CBP is placed on an evaporation dish with Ir(btp)$_2$acac, in which the ratio between CBP and Ir(btp)$_2$acac is 10:1. An evaporation process is performed thereafter at a rate of 0.2 nm/sec to form an organic luminescent layer 104 of 30 nm on the hole transport layer 112, in which the dopant within the organic luminescent layer 104 is Ir(btp)$_2$acac and the host material of the organic luminescent layer 104 is CBP.

Next, a hole-blocking layer 114 of 10 nm is coated on the organic luminescent layer 104. According to Experiment B1 of the present embodiment, the hole-blocking layer 114 is composed of the compound from Formula (2-3), and according to Experiment B2, the hole-blocking layer 114 is composed of the compound from Formula (4-1). By utilizing the materials selected, the present invention is able to retain the holes in the organic luminescent layer 104 and improve the transformation efficiency for illumination of the device.

Next, an AlQ$_3$ layer is coated on the hole-blocking layer 114, in which the AlQ$_3$ layer is utilized as the electron transport layer 110. The thickness of the electron transport layer 110 is 30 nm, and the evaporation process performed is maintained at 0.2 nm/sec. Next, a lithium fluoride of 0.5 nm is coated on the electron transport layer 110, in which the lithium fluoride is utilized as the electron injection layer 110a.

Subsequently, an aluminum layer of 120 nm, functions as the cathode 106, and is formed on the electron injection layer 110a to complete the fabrication of the electroluminescent device.

Experiment B3

Experiment B3 discloses a method for fabricating an organic luminescent device having a six layer organic structure. Similar to the comparative example, a glass substrate 100 having a dimension of 45 mm×45 mm is first provided. Next, an indium tin oxide (ITO) layer having a thickness of 50 to 200 nm is coated on the glass substrate 100. Next, a photolithography and etching process is performed to form the indium tin oxide layer into a plurality of luminescent patterns. Each of the luminescent patterns has a dimension of 3 mm×3 mm, in which the patterns are utilized as an anode 102. Next, a vacuum evaporation process is performed at a vacuum degree of $10^{-6}$ Pa to coat a hole injection layer 112a of 50 nm on the surface of the anode 102, in which the hole injection layer 112a is composed of 4,4',4"-Tris(N-(2-naphthyl)-N-phenyl-amino)-triphenylamine (2-NTNATA). Next, a vacuum evaporation process is performed to coat a hole transport layer 112 of 20 nm on the surface of the hole injection layer 112a, in which the hole transport layer 112 is composed of N4,N4'-Di-naphthalen-1-yl-N4,N4'-diphenyl-biphenyl-4,4'-diamine (NPB).

Next, the material from Formula (2-3) is placed on an evaporation dish with Ir(btp)$_2$acac, in which the ratio between the material and Ir(btp)$_2$acac is 10:1. The evaporation process is performed at a rate of 0.2 nm/sec to form an organic luminescent layer 104 of 30 nm on the hole transport layer 112, in which the dopant within the organic luminescent layer 104 is Ir(btp)$_2$acac and the host material of the organic luminescent layer 104 is the compound from Formula (2-3).

Next, a hole-blocking layer 114 of 10 nm is coated on the organic luminescent layer 104. According to Experiment B3 of the present embodiment, the hole-blocking layer 114 is composed of the compound from Formula (2-3). By utilizing the materials selected, the present invention is able to retain the holes in the organic luminescent layer 104 and improve the illumination of the device. Hence, in the present example, the host material of both hole-blocking layer 114 and organic luminescent layer is the compound from Formula (2-3).

Next, an AlQ$_3$ layer is coated on the hole-blocking layer 114, in which the AlQ$_3$ layer is utilized as the electron transport layer 110. The thickness of the electron transport layer 110 is 30 nm, and the evaporation process performed is maintained at 0.2 nm/sec. Next, a lithium fluoride of 0.5 nm is coated on the electron transport layer 110, in which the lithium fluoride is utilized as the electron injection layer 110a.

Subsequently, an aluminum layer of 120 nm, functions as the cathode 106, and is formed on the electron injection layer 110a to complete the fabrication of the electroluminescent device.

Experiment H1

Experiment H1 discloses a method for fabricating an organic luminescent device having a six layer organic structure. Similar to the comparative example, a glass substrate 100 having a dimension of 45 mm×45 mm is first provided. Next, an indium tin oxide (ITO) layer having a thickness of 50 to 200 nm is coated on the glass substrate 100. Next, a photolithography and etching process is performed to form the indium tin oxide layer into a plurality of luminescent patterns. Each of the luminescent patterns has a dimension of 3 mm×3 mm, in which the patterns are utilized as an anode 102. Next, a vacuum evaporation process is performed at a vacuum degree of 10$^{-6}$ Pa to coat a hole injection layer 112a of 50 nm on the surface of the anode 102, in which the hole injection layer 112a is composed of 4,4',4''-Tris(N-(2-naphthyl)-N-phenyl-amino)-triphenylamine (2-NTNATA). Next, a vacuum evaporation process is performed to coat a hole transport layer 112 of 20 nm on the surface of the hole injection layer 112a, in which the hole transport layer 112 is composed of N4,N4'-Di-naphthalen-1-yl-N4,N4'-diphenyl-biphenyl-4,4'-diamine (NPB).

Next, the material from Formula (2-3) is placed on an evaporation dish with Ir(btp)$_2$acac, in which the ratio between the material and Ir(btp)$_2$acac is 10:1. An evaporation process is performed thereafter at a rate of 0.2 nm/sec to form an organic luminescent layer 104 of 30 nm on the hole transport layer 112, in which the dopant within the organic luminescent layer 104 is Ir(btp)$_2$acac and the host material of the organic luminescent layer 104 is the compound from Formula (2-3).

Next, a hole-blocking layer 114 of 10 nm is coated on the organic luminescent layer 104, in which the hole-blocking layer 114 is composed of 2,9-dimethyl-4,7-diphenyl-1,10-phenanthroline (BCP).

Next, an AlQ$_3$ layer is coated on the hole-blocking layer 114, in which the AlQ$_3$ layer is utilized as the electron transport layer 110. The thickness of the electron transport layer 110 is 30 nm, and the evaporation process performed is maintained at 0.2 nm/sec. Next, a lithium fluoride of 0.5 nm is coated on the electron transport layer 110, in which the lithium fluoride is utilized as the electron injection layer 110a.

Subsequently, an aluminum layer of 120 nm, functions as the cathode 106, and is formed on the electron injection layer 110a to complete the fabrication of the electroluminescent device.

Experiment H2

Experiment H2 discloses a method for fabricating an organic luminescent device having a six layer organic structure. According to the present embodiment, a material from Formula (3-54) is first placed on an evaporation dish with Ir(btp)$_2$acac, in which the ratio between the material and Ir(btp)$_2$acac is 10:1. Next, an evaporation process is performed at a rate of 0.2 nm/sec to form an organic luminescent layer 104 of 30 nm on the hole transport layer 112, in which the dopant within the organic luminescent layer 104 is Ir(btp)$_2$acac and the host material of the organic luminescent layer 104 is the compound from Formula (3-54). Other steps of the fabrication processes of the present embodiment are identical to the ones described in Experiment H1.

Experiment H3

Experiment H3 discloses a method for fabricating an organic luminescent device having a six layer organic structure. According to the present embodiment, a material from Formula (3-55) is first placed on an evaporation dish with Ir(btp)$_2$acac, in which the ratio between the material and Ir(btp)$_2$acac is 10:1. Next, an evaporation process is performed at a rate of 0.2 nm/sec to form an organic luminescent layer 104 of 30 nm on the hole transport layer 112, in which the dopant within the organic luminescent layer 104 is Ir(btp)$_2$acac and the host material of the organic luminescent layer 104 is the compound from Formula (3-55). Other steps of the fabrication processes of the present embodiment are identical to the ones described in Experiment 1.

Experiment H4

Experiment H4 discloses a method for fabricating an organic luminescent device having a six layer organic structure. According to the present embodiment, a material from Formula (4-1) is first placed on an evaporation dish with Ir(btp)$_2$acac, in which the ratio between the material and Ir(btp)$_2$acac is 10:1. Next, an evaporation process is performed at a rate of 0.2 nm/sec to form an organic luminescent layer 104 of 30 nm on the hole transport layer 112, in which the dopant within the organic luminescent layer 104 is Ir(btp)$_2$acac and the host material of the organic luminescent layer 104 is the compound from Formula (4-1). Other steps of the fabrication processes of the present embodiment are identical to the ones described in Experiment H1.

In order to demonstrate the effect of the material of the present invention, tests involving the phosphorescent property, light property, and thermal stability between the conventional luminescent material and luminescent material of the present invention are discussed below.

(1) Phosphorescent Property

Figure 7:
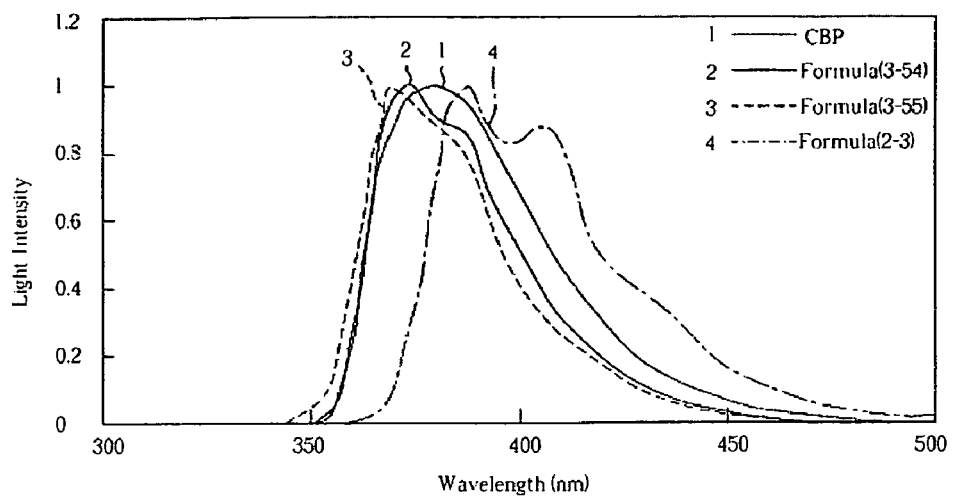
FIG. 7 is a comparative diagram illustrating the phosphorescent property between the conventional luminescent material and the luminescent material of the present invention.
Figure 8A:
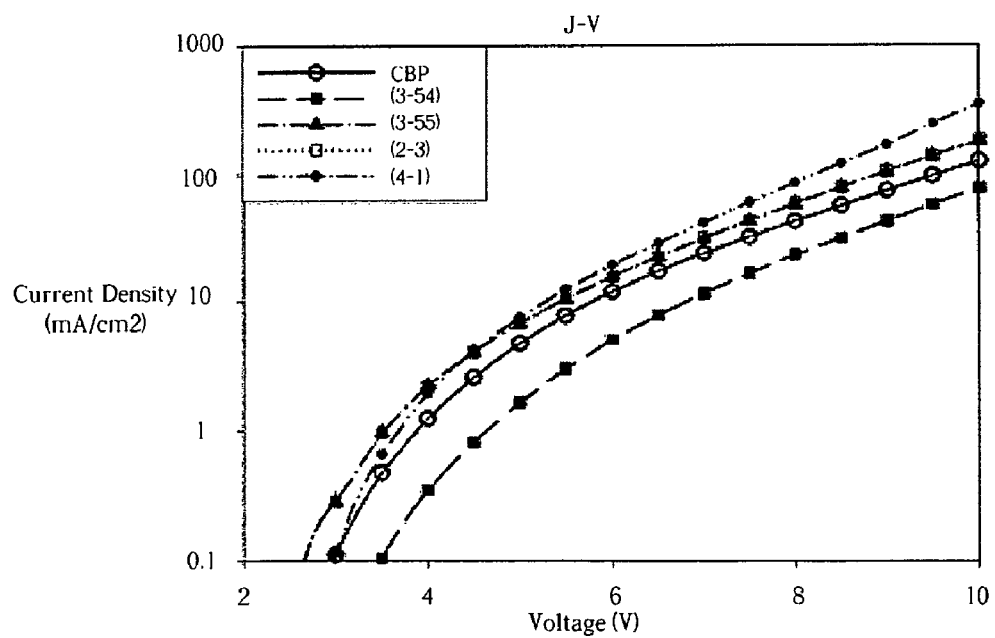
FIG. 8A is a comparative diagram illustrating a relationship of voltage and current density between the conventional luminescent material and the luminescent material of the present invention as the materials are utilized as the host material of the luminescent device.
Figure 8B:
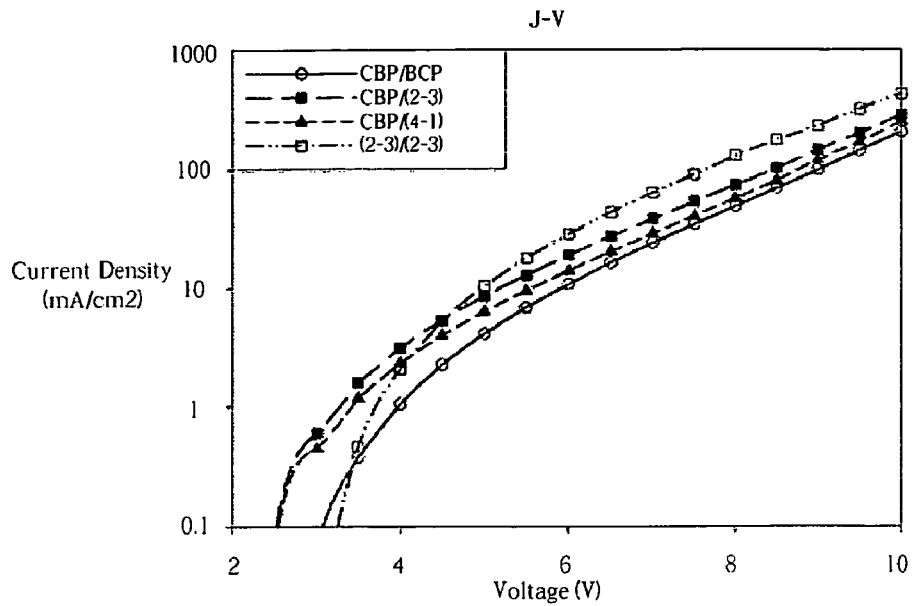
FIG. 8B is a comparative diagram illustrating a relationship of voltage and current density between the conventional luminescent material and the luminescent material of the present invention as the materials are utilized as the hole-blocking layer of the luminescent device.
Figure 9A:
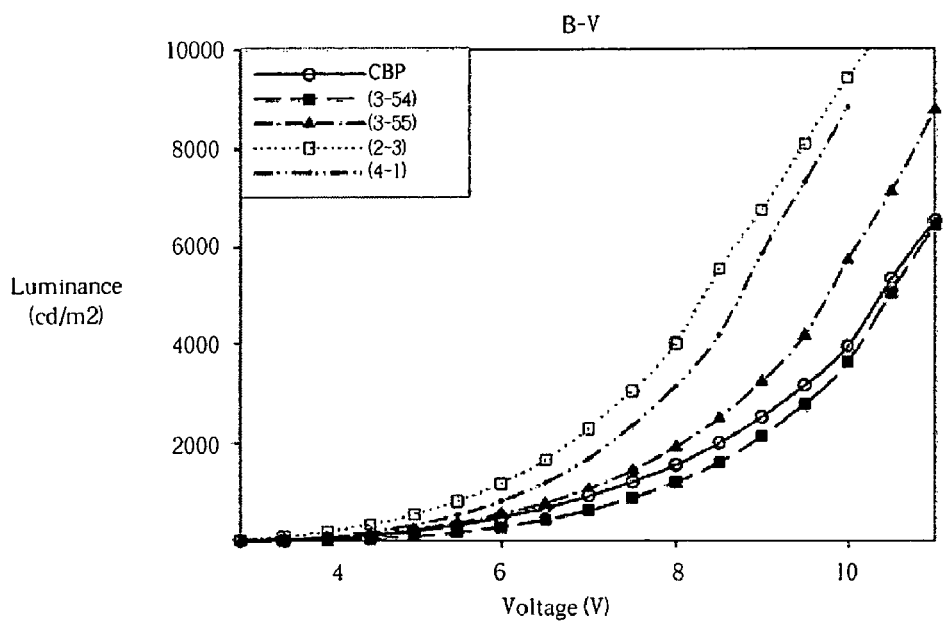
FIG. 9A is a comparative diagram illustrating a relationship of voltage and luminance between the conventional luminescent material and the luminescent material of the present invention as the materials are utilized as the host material of the luminescent device.
Figure 9B:
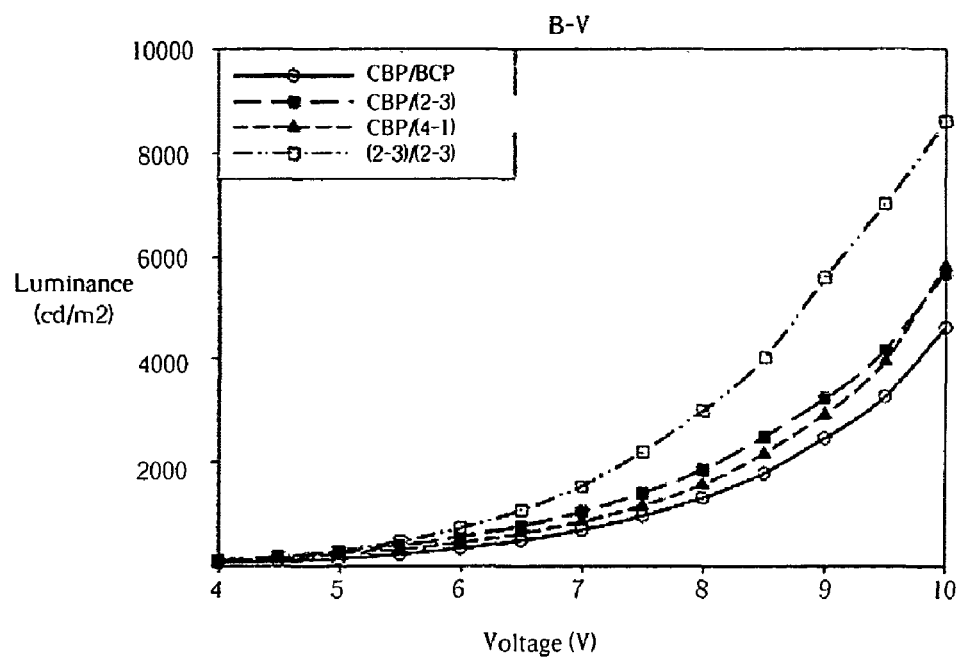
FIG. 9B is a comparative diagram illustrating a relationship of voltage and luminance between the conventional luminescent material and the luminescent material of the present invention as the materials are utilized as the hole-blocking layer of the luminescent device.

FIG. 7 is a comparative diagram illustrating the phosphorescent property between the conventional luminescent material and the luminescent material of the present invention. As shown in FIG. 7, the wavelengths of the compound from Formula (2-3), (3-54), and (3-55) are between 380 nm and 410 nm, as indicated by curves 2, 3, and 4, whereas the wavelength of CBP is around 390 nm, as indicated by curve 1. In other words, by applying the material of the present invention on the organic luminescent layer, the phosphorescent intensity of the electroluminescent device will be comparable to the device utilizing the conventional CBP material.

(2) Light Property

FIGS. 8A, 8B, 9A, and 9B are comparative diagrams illustrating a relationship of voltage and current density, and voltage and luminance between the conventional luminescent material and luminescent material of the present invention. As shown in FIGS. 8A, 8B, 9A, and 9B, the performance of the current density and luminance of the present invention as the voltage increases is comparable to the performance of the current density and luminance of the conventional art of utilizing CBP material. Hence, the result indicates that the luminance performance of the organic luminescent layer or hole-blocking layer of the electroluminescent device utilizing the material of the present invention is comparable to the luminance performance of the device utilizing the conventional CBP material.

(3) Thermal Stability

Figure 10:
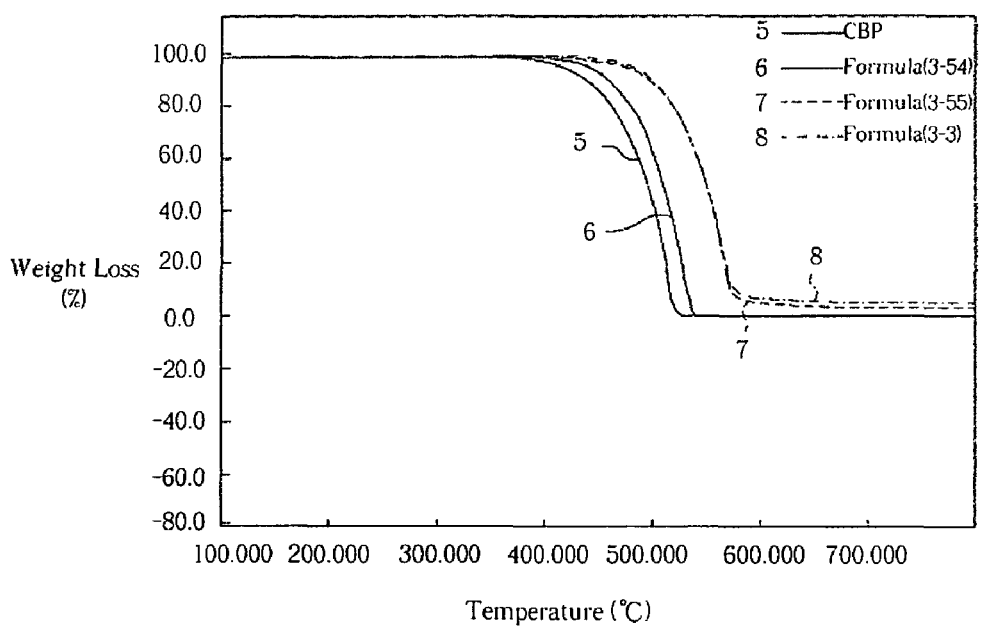
FIG. 10 is a diagram illustrating the thermal stability between the conventional luminescent material and luminescent material of the present invention.

Due to the fact that the temperature of the organic electroluminescent device increase as external voltage is applied, poor thermal stability caused by the internal material of the device, especially the material of the luminescent layer, will result in problem such as decomposition of the material or transformation of the molecular film. These problems will ultimately degrade the heat dissipating ability, cause color distortion, and reduce life expectancy of the device. Hence, a thermogravimetric analysis is performed to measure the thermal stability of the conventional luminescent material and the luminescent material of the present invention. Preferably, a Thermo gravimetry analyzer (TGA) from Perkin Elmer having a model number of S-II is utilized to obtain a sample of 2 to 3 grams. FIG. 10 is a diagram illustrating the thermal stability between the conventional luminescent material and luminescent material of the present invention. If a 5% weight loss of the sample being tested is set as an index of thermal decomposition (Td) temperature, the thermal decomposition temperatures measured for Formula (2-3), (3-54), (3-55), and (4-1) will be 508° C., 473° C., 503° C., and 411° C. respectively, as indicated by curves 6, 7, and 8 in the figure, and the thermal decomposition temperature for CBP will be 447° C., as indicated by curve 5. Since the thermal decomposition temperatures of Formula (2-3), (3-54), (3-55), and (4-1) are greater than the thermal decomposition temperature of CBP, the thermal stability of the compounds from Formula (2-3), (3-54), (3-55), and (4-1) is thus significantly greater than the thermal stability of CBP. Hence, comparing to the electroluminescent device utilizing conventional CBP material, the fact that the material of the present invention does not crystallize easily and is able to significantly increase the luminance performance and life expectancy of the device.

Overall, by utilizing the material of the present invention to fabricate the organic luminescent layer of the organic electroluminescent device, the device will not only have the advantage of high thermal stability, but also have improved luminance performance. The material disclosed by the present invention also applies to organic light emitting diode displays. Specifically, the film characteristics of the material further increases the luminance performance and life expectancy of the device, as the material does not crystallize easily, and by incorporating the material of the present invention into the hole-blocking layer of the electroluminescent device, the luminance performance can be increased significantly.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:
1. An electroluminescent device, comprising:
a substrate;
an anode, disposed on the substrate;
an organic luminescent layer, disposed on the anode; and
a cathode, disposed on the organic luminescent layer, wherein the organic luminescent layer comprises a fluorene compound as Formula (1):

Formula (1):

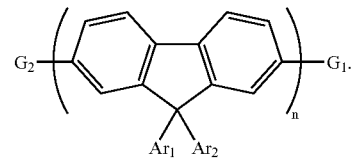

wherein Ar1 and Ar2 each represents an aryl group having from 6 to 12 carbon atoms; G1 and G2 each represents an aryl group having from 6 to 24 carbon atoms, a boron group, or a silyl group having from 3 to 18 atoms; and wherein n is an integer from 1 to 4.

2. The electroluminescent device of claim 1, wherein each of Ar1 and Ar2 is selected from the group consisting of: phenyl, biphenyl, tolyl, naphthyl, anthranyl, and phenanthryl.

3. The electroluminescent device of claim 1, wherein the boron group comprises an aryl group having from 6 to 12 atoms.

4. The electroluminescent device of claim 1 further comprising a hole-blocking layer, disposed between the cathode and the organic luminescent layer.

5. The electroluminescent device of claim 4, wherein the hole-blocking layer comprises the compound of formula (1).

6. The electroluminescent device of claim 4 further comprising an electron transport layer, disposed between the hole-blocking layer and the cathode.

7. The electroluminescent device of claim 6 further comprising an electron injection layer, disposed between the electron transport layer and the cathode.

8. The electroluminescent device of claim 1 further comprising a hole transport layer, disposed between the anode and the organic luminescent layer.

9. The electroluminescent device of claim 8 further comprising a hole injection layer, disposed between the anode and the hole transport layer.

10. The electroluminescent device of claim 1, wherein the organic luminescent layer further comprises a dopant.

11. The electroluminescent device of claim 10, wherein the dopant is selected from the group consisting of at least two of: FIr(pic)$_3$, Ir(ppy)$_3$, Ir(m-ppy)$_3$, Ir(btp)$_2$(acac), Ir(btp)$_3$, Ir(DBQ)$_2$(acac), PtOEP, Ir(tpy)$_2$(pz2BEt$_2$), Ir(tpy)$_2$(pz2BPh2), Ir(piq)$_2$(acac), Ir(piq-F)$_2$(acac), Ir(pbq-F)$_2$(acac), Ir(piq-F)$_3$, Ir(piq)$_3$, and Ir(pbq)$_3$, and the formula of the dopants comprises:

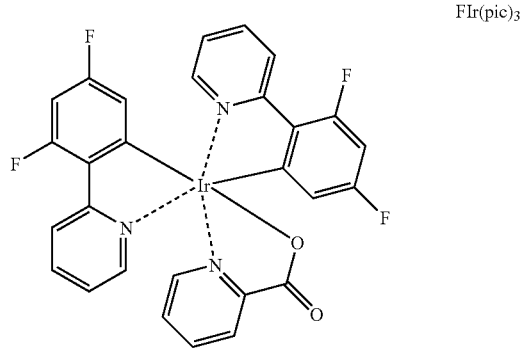

FIr(pic)$_3$

-continued
Ir(ppy)₃
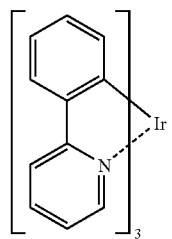
Ir(m-ppy)₃
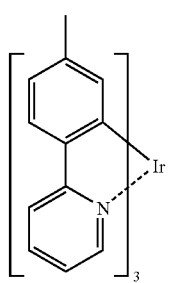
Ir(btp)₂acac
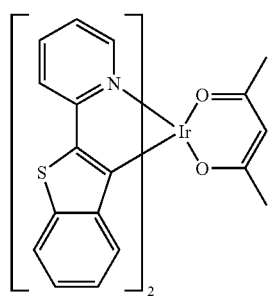
Ir(btp)₃
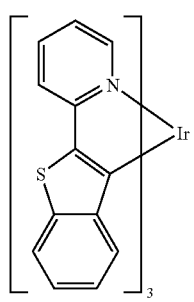
Ir(DBQ)₂acac
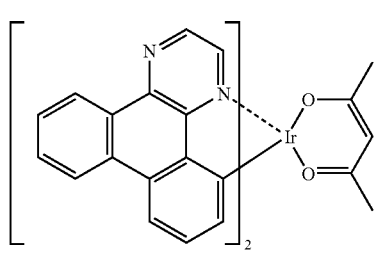
-continued
PtOEP
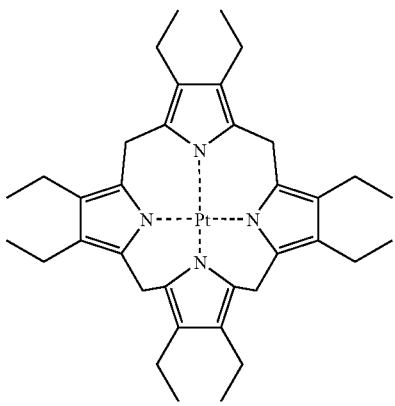
Ir(tpy)₂(pz2BEt2)
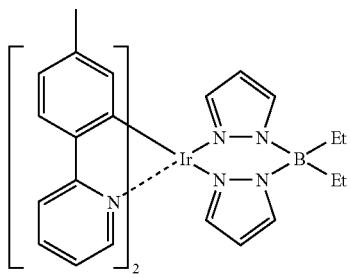
Ir(tpy)₂(pz2BPh2)
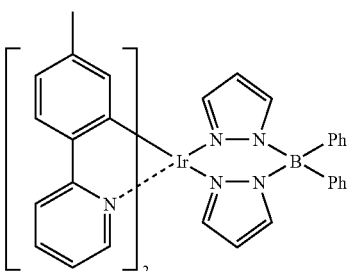
Ir(piq)₂(acac)
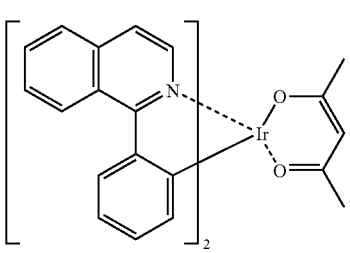
Ir(piq-F)₂(acac)
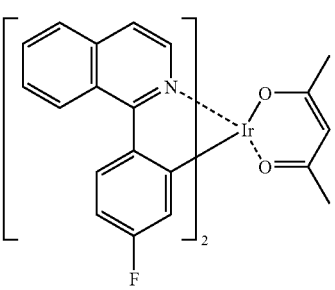

-continued

Ir(pbq-F)₂(acac)

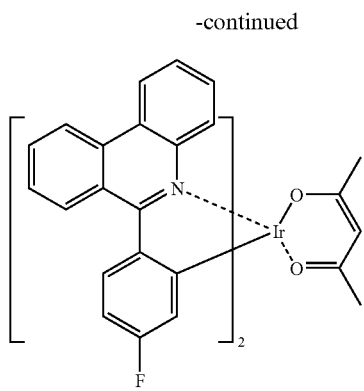

Ir(piq-F)₃

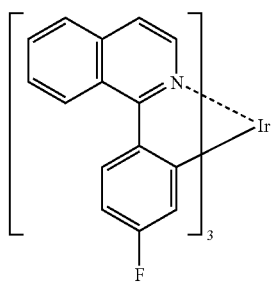

Ir(piq)₃

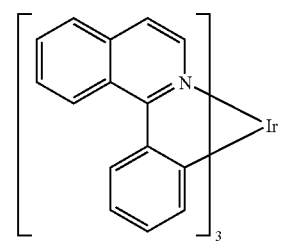

Ir(pbq)₃

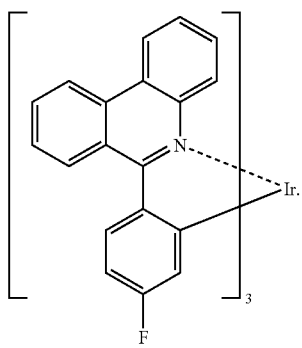

12. An electroluminescent device, comprising:
a substrate;
an anode, disposed on the substrate;
an organic luminescent layer, disposed on the anode; and
a cathode, disposed on the organic luminescent layer, wherein the organic luminescent layer comprises a fluorene compound as Formula (1):

Formula (1):

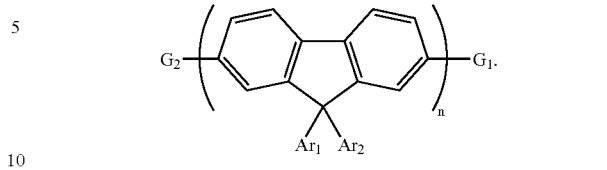

wherein Ar1 and Ar2 each represents an aryl group having from 6 to 12 carbon atoms; G1 and G2 each represents a boron group; and wherein n is an integer from 1 to 4.

13. The electroluminescent device of claim 12, wherein the boron group comprises an aryl group having from 6 to 12 atoms.

14. The electroluminescent device of claim 12, further comprising a hole-blocking layer, disposed between the cathode and the organic luminescent layer; and wherein the hole-blocking layer comprises the compound of formula (1).

15. The electroluminescent device of claim 12, further comprising
a hole-blocking layer, disposed between the cathode and the organic luminescent layer;
an electron transport layer, disposed between the hole-blocking layer and the cathode; and
an electron injection layer, disposed between the electron transport layer and the cathode.

16. An electroluminescent device, comprising:
a substrate;
an anode, disposed on the substrate;
an organic luminescent layer, disposed on the anode; and
a cathode, disposed on the organic luminescent layer, wherein the organic luminescent layer comprises a fluorene compound as Formula (1):

Formula (1):

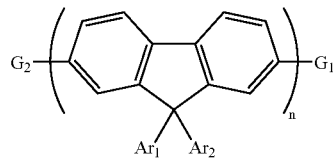

wherein Ar1 and Ar2 each represents an aryl group having from 6 to 12 carbon atoms; G1 and G2 each represents a silyl group having from 3 to 18 atoms or a triphenyl silyl group; and wherein n is an integer from 1 to 4.

17. An electroluminescent device of claim 16, wherein G1 and G2 each represents a silyl group having from 3 to 18 atoms.

18. The electroluminescent device of claim 17, further comprising a hole-blocking layer, disposed between the cathode and the organic luminescent layer; and wherein the hole-blocking layer comprises the compound of formula (1).

19. The electroluminescent device of claim 17, further comprising
a hole-blocking layer, disposed between the cathode and the organic luminescent layer;
an electron transport layer, disposed between the hole-blocking layer and the cathode; and
an electron injection layer, disposed between the electron transport layer and the cathode.

* * * * *